(12) United States Patent
Locke et al.

(10) Patent No.: US 12,274,823 B2
(45) Date of Patent: Apr. 15, 2025

(54) MEDICAL SYSTEM AND DRESSING FOR USE UNDER COMPRESSION

(71) Applicant: Solventum Intellectual Properties Company, Maplewood, MN (US)

(72) Inventors: Christopher Brian Locke, Bournemouth (GB); Justin Alexander Long, Lago Vista, TX (US); Benjamin Locke, Bournemouth (GB); Benjamin Andrew Pratt, Poole (GB); Thomas Alan Edwards, Hampshire (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 87 days.

(21) Appl. No.: 18/134,937

(22) Filed: Apr. 14, 2023

(65) Prior Publication Data
US 2023/0270597 A1    Aug. 31, 2023

Related U.S. Application Data

(62) Division of application No. 16/717,754, filed on Dec. 17, 2019, now Pat. No. 11,654,056, which is a (Continued)

(51) Int. Cl.
*A61F 13/01* (2024.01)
*A61M 1/00* (2006.01)
*A61F 13/05* (2024.01)

(52) U.S. Cl.
CPC ....... *A61M 1/913* (2021.05); *A61F 13/01029* (2024.01); *A61F 13/05* (2024.01); *A61M 1/915* (2021.05); *A61M 1/96* (2021.05)

(58) Field of Classification Search
CPC ............ A61F 13/00068; A61F 13/0216; A61F 13/00029; A61F 13/0206; A61F 13/022; A61F 13/025
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for PCT/US2016/059905, mailed Jan. 26, 2017.

(Continued)

*Primary Examiner* — Susan S Su

(57) ABSTRACT

In some illustrative examples, a bridge suitable for treating a tissue site may include a bridge sealing member and one or more bridge wicking layers. The bridge sealing member may extend along a length of the bridge, and may define an internal passageway in fluid communication between a receiving end of the bridge and a transmitting end of the bridge. The one or more bridge wicking layers may be disposed within the internal passageway of the bridge sealing member. Other apparatus, systems, and methods are disclosed.

7 Claims, 16 Drawing Sheets

Related U.S. Application Data division of application No. 15/356,063, filed on Nov. 18, 2016, now Pat. No. 10,548,777.

(60) Provisional application No. 62/257,903, filed on Nov. 20, 2015.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| D746,435 S | 12/2015 | Armstrong et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0101940 A1 | 5/2005 | Radl et al. |
| 2006/0079852 A1 | 4/2006 | Bubb et al. |
| 2007/0185463 A1 | 8/2007 | Mulligan |
| 2008/0195017 A1 | 8/2008 | Robinson et al. |
| 2008/0271804 A1 | 11/2008 | Biggie et al. |
| 2008/0275409 A1 | 11/2008 | Kane et al. |
| 2009/0221977 A1 | 9/2009 | Blott et al. |
| 2009/0227969 A1 | 9/2009 | Jaeb et al. |
| 2010/0137775 A1 | 6/2010 | Hu et al. |
| 2010/0160853 A1 | 6/2010 | Smith et al. |
| 2010/0185163 A1 | 7/2010 | Heagle |
| 2010/0324510 A1 | 12/2010 | Andresen et al. |
| 2010/0324516 A1 | 12/2010 | Braga et al. |
| 2011/0230849 A1 | 9/2011 | Coulthard et al. |
| 2012/0116334 A1 | 5/2012 | Albert et al. |
| 2012/0215193 A1 | 8/2012 | Siniaguine et al. |
| 2013/0066284 A1 | 3/2013 | Croizat et al. |
| 2013/0096518 A1 | 4/2013 | Hall et al. |
| 2013/0123722 A1 | 5/2013 | Pratt et al. |
| 2013/0144230 A1 | 6/2013 | Wu et al. |
| 2013/0310809 A1 | 11/2013 | Armstrong et al. |
| 2014/0163491 A1 | 6/2014 | Schuessler et al. |
| 2014/0276490 A1 | 9/2014 | Locke et al. |
| 2014/0330224 A1 | 11/2014 | Albert et al. |
| 2014/0350494 A1 | 11/2014 | Hartwell et al. |
| 2015/0080788 A1 | 3/2015 | Blott et al. |

(56) References Cited

U.S. PATENT DOCUMENTS

| | | | |
|---|---|---|---|
| 2015/0141941 A1 | 5/2015 | Allen et al. |
| 2015/0216733 A1 | 8/2015 | Allen et al. |
| 2015/0245950 A1 | 9/2015 | Locke et al. |
| 2016/0106892 A1 | 4/2016 | Hartwell |
| 2016/0120706 A1 | 5/2016 | Collinson et al. |
| 2016/0262942 A1 | 9/2016 | Riesinger |
| 2016/0287765 A1 | 10/2016 | Canner et al. |
| 2016/0339158 A1 | 11/2016 | Collinson et al. |
| 2017/0189236 A1 | 7/2017 | Locke et al. |
| 2018/0325741 A1 | 11/2018 | Lewis et al. |
| 2019/0015258 A1 | 1/2019 | Gowans et al. |
| 2019/0192350 A1 | 6/2019 | Gowans et al. |
| 2019/0343687 A1 | 11/2019 | Locke et al. |
| 2020/0121510 A1 | 4/2020 | Hartwell et al. |
| 2021/0401628 A1 | 12/2021 | Gowans et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3195885 A1 | 7/2017 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005/051461 A1 | 6/2005 |
| WO | 2009002260 A1 | 12/2008 |
| WO | 2009089016 A1 | 7/2009 |
| WO | 2009126102 A1 | 10/2009 |
| WO | 2011087871 A2 | 7/2011 |
| WO | 2012142002 A1 | 10/2012 |
| WO | 2013032539 A1 | 3/2013 |
| WO | 2014184674 A2 | 11/2014 |
| WO | 2015/050749 A1 | 4/2015 |
| WO | 2016/126444 A1 | 8/2016 |
| WO | 2017087163 A1 | 5/2017 |
| WO | 2017196888 A1 | 11/2017 |

OTHER PUBLICATIONS

International Search Report and Written Opinion for PCT/US2017/062035, mailed Feb. 7, 2018.
International Search Report and Written Opinion for Corresponding Application No. PCT/US2018/048527, mailed Dec. 19, 2018.
International Search Report and Written Opinion for corresponding Application No. PCT/US2018/055131, mailed Mar. 18, 2019.
International Search Report and Written Opinion for Corresponding Application No. PCT/US2019/020308, mailed May 10, 2019.
Japanese Notice of Rejection Corresponding to Application No. 2019-513393, mailed Aug. 3, 2021.
U.S. Non-Final Office Action Corresponding to U.S. Appl. No. 16/755,814, mailed Jan. 31, 2022.
U.S. Non-Final Office Action Corresponding to U.S. Appl. No. 16/755,814, mailed Sep. 1, 2021.
U.S. Non-Final Office Action Corresponding to U.S. Appl. No. 17/046,023, mailed Jul. 12, 2022.
U.S. Non-Final Office Action Corresponding to U.S. Appl. No. 16/717,754, mailed Nov. 3, 2022.
U.S. Non-Final Office Action Corresponding to U.S. Appl. No. 16/717,609, mailed Jan. 20, 2023.
Visco A, Quattrocchi A, Nocita D, Montanini R, Pistone A. Polyurethane Foams Loaded with Carbon Nanofibers for Oil Spill Recovery: Mechanical Properties under Fatigue Conditions and Selective Absorption in Oil/Water Mixtures. Nanomaterials (Basel). p. 2.(Year: 2021).
U.S. Final Office Action Corresponding to U.S. Appl. No. 17/046,023 mailed Jan. 10, 2023.
Office Action for related U.S. Appl. No. 17/046,023, dated Jun. 7, 2024.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

(56) References Cited

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

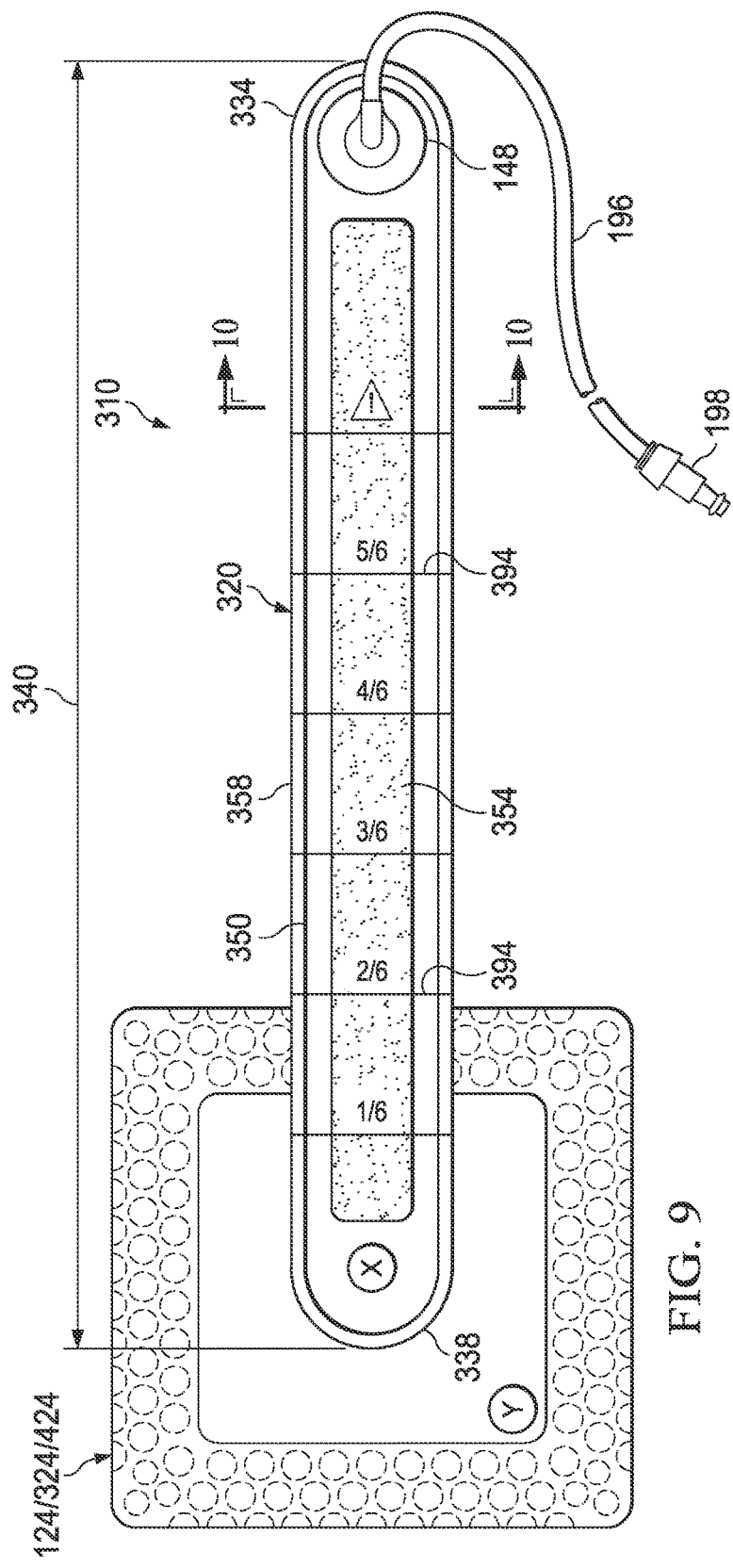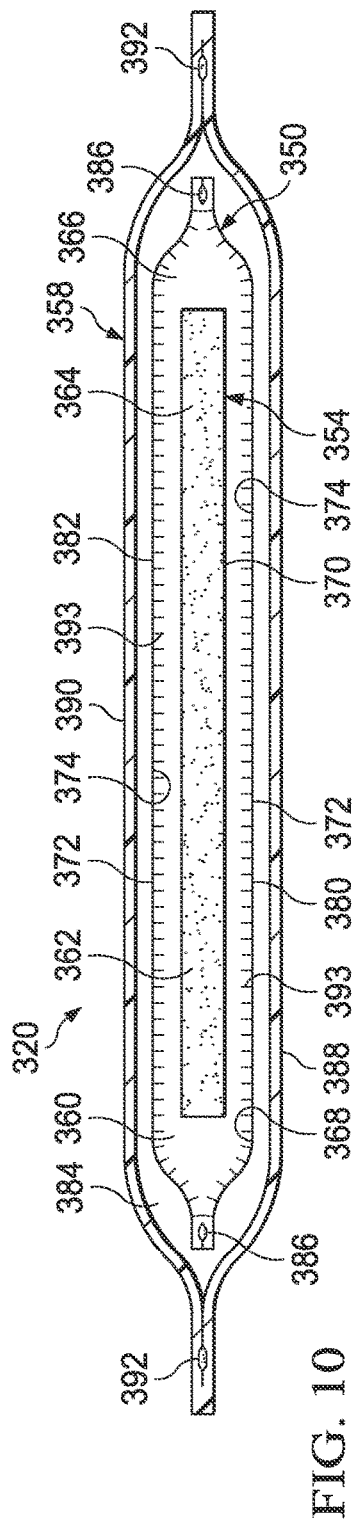
FIG. 9
FIG. 10

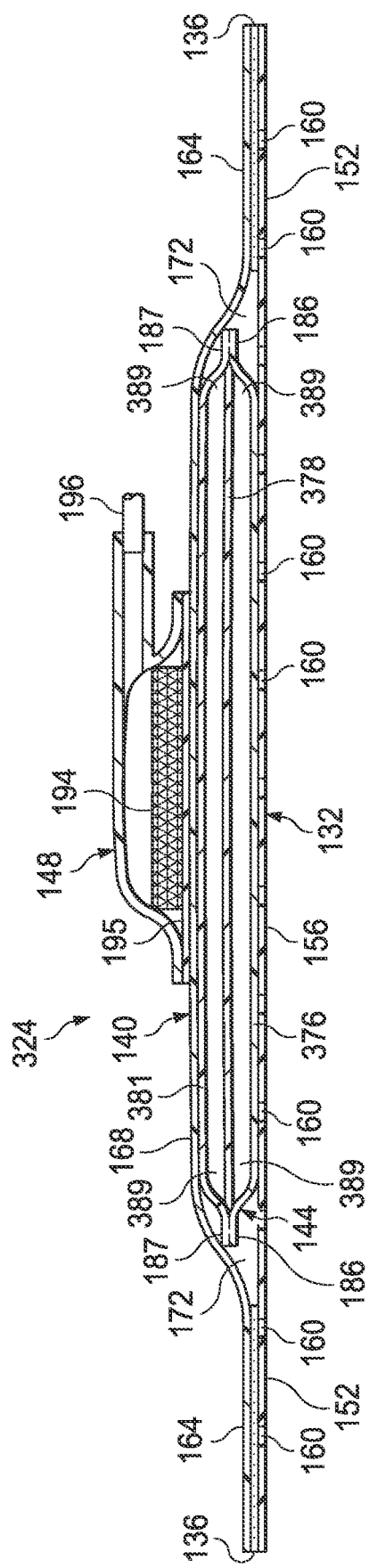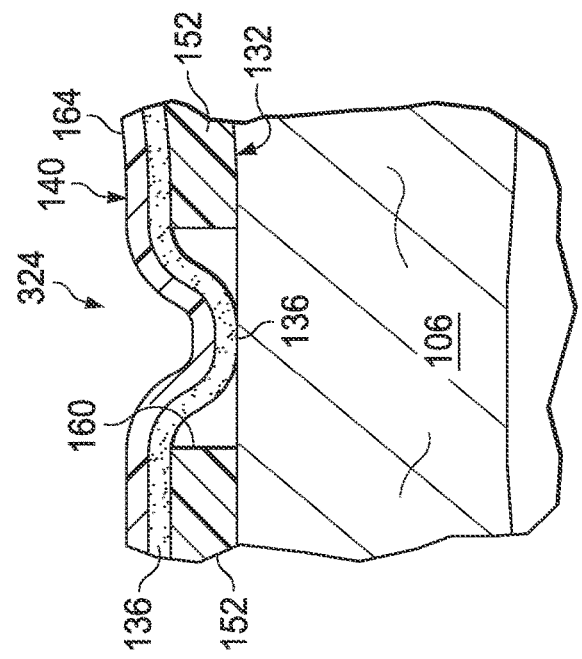
FIG. 14
FIG. 15

MEDICAL SYSTEM AND DRESSING FOR USE UNDER COMPRESSION

INCORPORATION BY REFERENCE

This application incorporates by reference the following disclosures in their entirety: U.S. Pat. No. 8,814,842, filed Mar. 11, 2011, titled DELIVERY-AND-FLUID-STORAGE BRIDGES FOR USE WITH REDUCED-PRESSURE SYSTEMS; U.S. Patent Publication No. 2014/0012213, filed Dec. 14, 2012, titled RELEASABLE MEDICAL DRAPES; U.S. Patent Publication No. 2015/0119833, filed Sep. 19, 2014, titled DRESSING WITH DIFFERENTIALLY SIZED PERFORATIONS.

RELATED APPLICATION

The present application is a divisional of U.S. patent application Ser. No. 16/717,754, entitled "MEDICAL SYSTEM AND DRESSING FOR USE UNDER COMPRESSION," filed Dec. 17, 2019, which is a divisional of U.S. patent application Ser. No. 15/356,063, entitled "MEDICAL SYSTEM AND DRESSING FOR USE UNDER COMPRESSION," filed Nov. 18, 2016, now U.S. Pat. No. 10,548,777; which claims the benefit, under 35 USC § 119(e), of the filing of U.S. Provisional Patent Application Ser. No. 62/257,903, entitled "MEDICAL SYSTEM WITH FLEXIBLE FLUID STORAGE BRIDGE," filed Nov. 20, 2015, all of which are incorporated herein by reference for all purposes.

FIELD

This application relates generally to medical treatment systems and, more particularly, but not by way of limitation, to dressings, systems, and methods that may be suitable for treating a tissue site.

BACKGROUND

Clinical studies and practice have shown that reducing pressure in proximity to a tissue site can augment and accelerate growth of new tissue at the tissue site. The applications of this phenomenon are numerous, but have been proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "reduced-pressure therapy." However, such treatment may also be known by other names including "negative-pressure therapy," "negative-pressure wound therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a tissue site. Together, these benefits can increase development of granulation tissue and reduce healing times. Improvements to therapy systems, components, and processes may benefit manufacturers, healthcare providers, and patients.

SUMMARY

In some illustrative, non-limiting examples, a bridge assembly for treating a tissue site may include a storage bridge. The storage bridge may include a receiving end and a transmitting end separated by a length. The storage bridge may include a bridge envelope, a bridge absorbent, and a bridge sealing member. The bridge envelope may extend along the length of the storage bridge and may define an internal volume. The bridge absorbent may be disposed within the internal volume of the bridge envelope. The bridge absorbent may include a volume that is less than the internal volume of the bridge envelope. The bridge sealing member may encapsulate the bridge envelope and may define an internal passageway in fluid communication between the receiving end and the transmitting end.

In some illustrative, non-limiting examples, a storage bridge for treating a tissue site may include a receiving end and a transmitting end separated by a length. Further, the storage bridge may include a bridge envelope, a bridge absorbent, and a bridge sealing member. The bridge envelope may extend along the length of the storage bridge, and may define an internal volume. Further, the bridge envelope may include a fluid acquisition surface and a fluid distribution surface positioned opposite the fluid acquisition surface. The fluid distribution surface may face the internal volume. The bridge absorbent may be disposed within the bridge envelope. At least a portion of the bridge absorbent may be spaced apart from the fluid distribution surface of the bridge envelope. The bridge sealing member may encapsulate the bridge envelope, and may define an internal passageway in fluid communication between the receiving end and the transmitting end.

In some illustrative, non-limiting examples, a storage bridge for treating a tissue site may include a receiving end and a transmitting end separated by a length. Further, the storage bridge may include a first bridge wicking layer, a second bridge wicking layer, a bridge absorbent, and a bridge sealing member. The first bridge wicking layer may extend along the length of the storage bridge, and may comprise a fluid acquisition surface and a fluid distribution surface. The fluid distribution surface may be positioned on an opposite side of the first bridge wicking layer from the fluid acquisition surface. The second bridge wicking layer may extend along the length of the storage bridge, and may comprise a fluid acquisition surface and a fluid distribution surface. The fluid distribution surface may be positioned on an opposite side of the second bridge wicking layer from the fluid acquisition surface. A periphery of the second bridge wicking layer may be coupled to a periphery of the first bridge wicking layer to define an internal volume. The bridge absorbent may be disposed within the internal volume between the first bridge wicking layer and the second bridge wicking layer. The fluid distribution surface of the first wicking layer and the second wicking layer may face the bridge absorbent. The bridge sealing member may include a substantially liquid impermeable and vapor permeable film. Further, the bridge sealing member may define an internal passageway in fluid communication between the receiving end and the transmitting end. The first bridge wicking layer and the second bridge wicking layer may be disposed within the internal passageway.

In some illustrative, non-limiting examples, a system for treating a tissue site may include a dressing, a storage bridge, a conduit interface, and a reduced-pressure source. The dressing may be for positioning at the tissue site, and may include a dressing sealing member and a dressing wicking layer. The dressing sealing member may be adapted to provide a sealed space between the dressing sealing member and the tissue site. The dressing wicking layer may be disposed in the sealed space. The storage bridge may include a receiving end and a transmitting end separated by a length.

The transmitting end may be adapted to be fluidly coupled to the dressing. Further, the storage bridge may include a bridge envelope, a bridge absorbent, and a bridge sealing member. The bridge envelope may extend along the length of the storage bridge, and may define an internal volume. The bridge absorbent may be disposed within the internal volume of the bridge envelope. The bridge sealing member may encapsulate the bridge envelope. The conduit interface may be adapted to be fluidly coupled to the receiving end of the storage bridge. Further, the conduit interface may be in fluid communication with the dressing through the storage bridge. The reduced-pressure source may be adapted to be positioned in fluid communication with the conduit interface.

In some illustrative, non-limiting examples, a system for treating a tissue site may include a dressing, a storage bridge, a conduit interface, and a reduced-pressure source. The dressing may be for positioning at the tissue site, and may include a dressing sealing member and a dressing manifold. The dressing sealing member may be adapted to provide a sealed space between the dressing sealing member and the tissue site. The dressing manifold may be disposed in the sealed space. The storage bridge may include a receiving end and a transmitting end separated by a length. The transmitting end may be adapted to be fluidly coupled to the dressing. Further, the storage bridge may include a bridge envelope, a bridge absorbent, and a bridge sealing member. The bridge envelope may extend along the length of the storage bridge, and may define an internal volume. The bridge absorbent may be disposed within the internal volume of the bridge envelope. The bridge sealing member may encapsulate the bridge envelope. The conduit interface may be adapted to be fluidly coupled to the receiving end of the storage bridge. The conduit interface may be in fluid communication with the dressing through the storage bridge. The reduced-pressure source may be adapted to be positioned in fluid communication with the conduit interface.

In some illustrative, non-limiting examples, a system for treating a tissue site may include a dressing, a storage bridge, a conduit interface, and a manual pump. The dressing may be for positioning at the tissue site, and may include a dressing sealing member and a dressing manifold. The dressing sealing member may be adapted to provide a sealed space between the dressing sealing member and the tissue site. The dressing manifold may be disposed in the sealed space. The storage bridge may include a receiving end and a transmitting end separated by a length. The transmitting end may be adapted to be fluidly coupled to the dressing. Further, the storage bridge may include a bridge envelope, a bridge absorbent, and a bridge sealing member. The bridge envelope may extend along the length of the storage bridge, and may define an internal volume. The bridge absorbent may be disposed within the internal volume of the bridge envelope. The bridge absorbent may have a volume that is at least 5 percent less than the internal volume of the bridge envelope. The bridge sealing member may encapsulate the bridge envelope. The conduit interface may be adapted to be fluidly coupled to the receiving end of the storage bridge. The conduit interface may be in fluid communication with the dressing through the storage bridge. The manual pump may be adapted to be positioned in fluid communication with the conduit interface.

In some illustrative, non-limiting examples, a method of treating a tissue site may include positioning a dressing at the tissue site. Further, the method may include fluidly coupling a transmitting end of a storage bridge to the dressing, and fluidly coupling a manual pump to a receiving end of the storage bridge. Further, the method may include manually activating the manual pump to cause fluid to move from the tissue site to the storage bridge through the dressing. Further, the method may include storing at least a portion of the fluid in the storage bridge. At least a portion of the fluid may be a liquid. Further, the method may include indicating a level of the fluid stored in the storage bridge with a plurality of fluid capacity indicators positioned along a length of the storage bridge.

In some illustrative, non-limiting examples, a system for treating a tissue site may include a dressing, a bridge, a conduit interface, and a reduced-pressure source. The dressing may be for positioning at the tissue site, and may include a dressing sealing member and one or more dressing wicking layers. The dressing sealing member may be adapted to provide a sealed space between the dressing sealing member and the tissue site. The one or more dressing wicking layers may be disposed in the sealed space. The bridge may include a receiving end and a transmitting end separated by a length. The transmitting end may be adapted to be fluidly coupled to the dressing. Further, the bridge may include a bridge sealing member, and one or more wicking members. The bridge sealing member may extend along the length, and may define an internal volume. The one or more bridge wicking layers may be disposed within the internal volume of the bridge sealing member. The conduit interface may be adapted to be fluidly coupled to the receiving end of the bridge. The conduit interface may be in fluid communication with the dressing through the bridge. The reduced-pressure source may be adapted to be positioned in fluid communication with the conduit interface.

In some examples, the bridge may additionally or alternatively include a bridge absorbent disposed within the internal volume of the bridge sealing member. The one or more dressing wicking layers may include at least a first dressing wicking layer, a second dressing wicking layer, and a third dressing wicking layer. In some embodiments, the one or more dressing wicking layers may include a first dressing wicking layer and a second dressing wicking layer. In some examples, a peripheral portion of the first dressing wicking layer is coupled to a peripheral portion of the third dressing wicking layer providing a wicking layer enclosure. The dressing may additionally or alternatively include a base layer and an adhesive. The base layer may have a periphery surrounding a central portion and a plurality of apertures disposed through the periphery and the central portion. The adhesive may be in fluid communication with the plurality of apertures at least in the periphery of the base layer. In some examples, the dressing sealing member may include a periphery and a central portion. The periphery of the dressing sealing member may be positioned proximate to the periphery of the base layer. The central portion of the dressing sealing member and the central portion of the base layer may define an enclosure. The one or more dressing wicking layers may be disposed in the enclosure. The dressing may additionally or alternatively include a base layer adapted to be positioned in contact with the tissue site. The base layer may include a non-adherent mesh. The one or more dressing wicking layers may be positioned between the base layer and the dressing sealing member.

In some examples, the one or more bridge wicking layers may include a first bridge wicking layer and a second bridge wicking layer. The first bridge wicking layer may have a surface area that is greater than a surface area of the second bridge wicking layer. The first bridge wicking layer may have a density that is greater than a density of the second bridge wicking layer. The first bridge wicking layer may be adapted to be positioned underneath the second bridge wicking layer.

In some examples, the one or more bridge wicking layers may include a fluid acquisition surface and a fluid distribution surface positioned opposite the fluid acquisition surface. The fluid distribution surface may face the internal volume of the bridge sealing member. The fluid distribution surface may include a plurality of longitudinal fibers oriented substantially in a longitudinal direction along the length of the bridge. The fluid acquisition surface may include a plurality of vertical fibers oriented substantially normal relative to the longitudinal fibers. The bridge sealing member may sealingly enclose the one or more bridge wicking layers between the receiving end and the transmitting end of the bridge. The bridge sealing member may include a substantially liquid impermeable and vapor permeable film. The system may additional or alternatively include a sealing apparatus adapted to be positioned about a transmitting end aperture and between the transmitting end and the dressing.

In some illustrative, non-limiting examples, a system for treating a tissue site may include a dressing, a bridge, a conduit interface, and a reduced-pressure source. The dressing may be for positioning at the tissue site, and may include a dressing sealing member and a dressing manifold. The dressing sealing member may be adapted to provide a sealed space between the dressing sealing member and the tissue site. The dressing manifold may be disposed in the sealed space. The bridge may include a receiving end and a transmitting end separated by a length. The transmitting end may be adapted to be fluidly coupled to the dressing. Further, the bridge may include a bridge sealing member, and one or more wicking members. The bridge sealing member may extend along the length, and may define an internal volume. The one or more bridge wicking layers may be disposed within the internal volume of the bridge sealing member. The conduit interface may be adapted to be fluidly coupled to the receiving end of the bridge. The conduit interface may be in fluid communication with the dressing through the bridge. The reduced-pressure source may be adapted to be positioned in fluid communication with the conduit interface.

In some illustrative, non-limiting examples, a system for treating a tissue site may include a dressing, a bridge, a conduit interface, and a manual pump. The dressing may be for positioning at the tissue site, and may include a dressing sealing member and one or more dressing wicking layers. The dressing sealing member may be adapted to provide a sealed space between the dressing sealing member and the tissue site. The one or more dressing wicking layers may be disposed in the sealed space. The bridge may include a receiving end and a transmitting end separated by a length. The transmitting end may be adapted to be fluidly coupled to the dressing. Further, the bridge may include a bridge sealing member, and one or more wicking members. The bridge sealing member may extend along the length, and may define an internal volume. The one or more bridge wicking layers may be disposed within the internal volume of the bridge sealing member. The conduit interface may be adapted to be fluidly coupled to the receiving end of the bridge. The conduit interface may be in fluid communication with the dressing through the bridge. The manual pump may be adapted to be positioned in fluid communication with the conduit interface.

In some illustrative, non-limiting examples, a method of treating a tissue site may include positioning a dressing at the tissue site. Further, the method may include fluidly coupling a transmitting end of a bridge to the dressing, and fluidly coupling a manual pump to a receiving end of the bridge. Further, the method may include manually activating the manual pump to cause fluid to move from the tissue site to the bridge through one or more dressing wicking layers of the dressing and to cause fluid to move through one or more bridge wicking layers of the bridge to the manual pump. Further, the method may include storing at least a portion of the fluid in the manual pump. At least a portion of the fluid may be a liquid.

In some illustrative, non-limiting examples, a bridge assembly for treating a tissue site may include a bridge. The bridge may include a receiving end and a transmitting end separated by a length. The bridge may include a bridge sealing member, and one or more bridge wicking layers. The bridge sealing member may extend along the length of the bridge and may define an internal passageway in fluid communication between the receiving end and the transmitting end. The one or more bridge wicking layers may be disposed within the internal passageway. The one or more bridge wicking layers may be configured to communicate fluid between the receiving end and the transmitting end of the bridge.

In some examples, the bridge assembly may alternatively or additionally include a bridge absorbent disposed within the internal passageway. The bridge absorbent may include a volume that is less than a volume of the internal passageway. The bridge assembly may alternatively or additionally include a conduit interface adapted to be fluidly coupled to the receiving end of the bridge. The conduit interface may be in fluid communication with the transmitting end through the bridge. The bridge assembly may alternatively or additionally include a fluid capacity indicator positioned along the length of the bridge. The bridge sealing member may encapsulate the one or more bridge wicking layers. The bridge sealing member may include a non-woven material. The one or more bridge wicking layers may be moveable within the internal passageway.

The one or more bridge wicking layers may include a first bridge wicking layer, a second bridge wicking layer, a third bridge wicking layer. A periphery of the first bridge wicking layer may be coupled to a periphery of the third bridge wicking layer. The second bridge wicking layer may be positioned between the first bridge wicking layer and the third bridge wicking layer. Each of the one or more bridge wicking layers may be comprised of a non-woven material. Each of the one or more bridge wicking layers may include a fluid acquisition surface and a fluid distribution surface positioned opposite the fluid acquisition surface. The fluid distribution surface of each of the one or more bridge wicking layers may face a first direction. The fluid acquisition surface of each of the one or more bridge wicking layers may face a second direction. The bridge sealing member may entirely surround the one or more bridge wicking layers. The bridge sealing member may include a substantially liquid impermeable film. The bridge sealing member may be a vapor permeable film. The bridge sealing member may include a breathable film. The bridge sealing member may include a first sealing layer and a second sealing layer. A periphery of the first sealing layer may be coupled to a periphery of the second sealing layer around the one or more bridge wicking layers.

In some examples, the one or more bridge wicking layers may include a first bridge wicking layer and a second bridge wicking layer. The first bridge wicking layer may have a surface area that is greater than a surface area of the second bridge wicking layer. The first bridge wicking layer may have a density that is greater than a density of the second bridge wicking layer. The first bridge wicking layer may be adapted to be positioned underneath the second bridge wicking layer.

In some illustrative, non-limiting examples, a bridge for treating a tissue site may include a receiving end and a transmitting end separated by a length. Further, the bridge may include a bridge sealing member, and one or more bridge wicking layers. The bridge sealing member may extend along the length of the bridge, and may define an internal passageway in fluid communication between the receiving end and the transmitting end. Further, the bridge sealing member may include a first sealing layer and a second sealing layer positioned opposite the first sealing layer. The one or more bridge wicking layers may be disposed within the bridge sealing member. At least a portion of the one or more bridge wicking layers may be spaced apart from the bridge sealing member. The one or more bridge wicking layers may include a first bridge wicking layer and a second bridge wicking layer. The first bridge wicking layer may have a surface area that is greater than a surface area of the second bridge wicking layer. The first bridge wicking layer may have a density that is greater than a density of the second bridge wicking layer. The first bridge wicking layer may be adapted to be positioned underneath the second bridge wicking layer.

In some examples, the bridge may additionally or alternatively include an absorbent disposed within the bridge sealing member. At least a portion of the absorbent may be spaced apart from the first sealing layer and the second sealing layer of the bridge sealing member. The bridge sealing member may entirely surround the one or more bridge wicking layers. The one or more bridge wicking layers may include a first bridge wicking layer, a second bridge wicking layer, and a third bridge wicking layer. A periphery of the first bridge wicking layer may be coupled to a periphery of the third bridge wicking layer. The second bridge wicking layer may be disposed between the first bridge wicking layer and the third bridge wicking layer. Each of the one or more bridge wicking layers may include of a non-woven material. Each of the one or more bridge wicking layers may include a fluid acquisition surface and a fluid distribution surface positioned opposite the fluid acquisition surface. The fluid distribution surface of each of the one or more bridge wicking layers may face a first direction. The fluid acquisition surface of each of the one or more bridge wicking layers may face a second direction. The bridge sealing member may include a substantially liquid impermeable and vapor permeable film.

In some illustrative, non-limiting examples, a bridge for treating a tissue site may include a receiving end and a transmitting end separated by a length. Further, the bridge may include a first set of one or more bridge wicking layers, a second set of one or more bridge wicking layers, and a bridge sealing member. The first set of one or more bridge wicking layers may extend along the length of the bridge, and may include a fluid acquisition surface and a fluid distribution surface. The fluid distribution surface may be positioned on an opposite side of at least one bridge wicking layer of the first set of one or more bridge wicking layers from the fluid acquisition surface. The second set of one or more bridge wicking layers may extend along the length of the storage bridge, and may include a fluid acquisition surface and a fluid distribution surface. The fluid distribution surface may be positioned on an opposite side of at least one bridge wicking layer of the second set of one or more bridge wicking layers from the fluid acquisition surface. A periphery of at least one bridge wicking layer of the second set of one or more bridge wicking layers may be coupled to a periphery of at least one bridge wicking layer of the first set of one or more bridge wicking layers to define an internal volume. The bridge sealing member may include a substantially liquid impermeable and vapor permeable film. Further, the bridge sealing member may define an internal passageway in fluid communication between the receiving end and the transmitting end. The first set of one or more bridge wicking layers and the second set of one or more bridge wicking layers may be disposed within the internal passageway.

In some embodiments, the bridge may alternatively or additionally a bridge absorbent disposed within the internal volume between the first set of one or more bridge wicking layers and the second set of one or more bridge wicking layers. The fluid distribution surface of the at least one bridge wicking layer of the first set of one or more bridge wicking layers and the at least one bridge wicking layer of the second set of one or more bridge wicking layers may face the bridge absorbent. At least a portion of the bridge absorbent may be spaced apart from the fluid distribution surface of the at least one bridge wicking layer of the first set of one or more bridge wicking layers and the at least one bridge wicking layer of the second set of one or more bridge wicking layers. The fluid distribution surface of the at least one bridge wicking layer of the first set of one or more bridge wicking layers and the at least one bridge wicking layer of the second set of one or more bridge wicking layers may include a plurality of longitudinal fibers oriented substantially in a longitudinal direction along the length. The fluid acquisition surface of the at least one bridge wicking layer of the first set of one or more bridge wicking layers and the at least one bridge wicking layer of the second set of one or more bridge wicking layers may include a plurality of vertical fibers oriented substantially normal relative to the longitudinal fibers.

In some illustrative, non-limiting examples, a bridge for treating a tissue site may include a receiving end and a transmitting end separated by a length. Further, the bridge may include a first bridge wicking layer, a second bridge wicking layer, and a bridge sealing member. The first bridge wicking layer may extend along the length of the bridge, and may include a fluid acquisition surface and a fluid distribution surface. The fluid distribution surface may be positioned on an opposite side of the first bridge wicking layer from the fluid acquisition surface. The second bridge wicking layer may extend along the length of the storage bridge, and may include a fluid acquisition surface and a fluid distribution surface. The fluid distribution surface may be positioned on an opposite side of the second bridge wicking layer from the fluid acquisition surface. A periphery of the second bridge wicking layer may be coupled to a periphery of the first bridge wicking layer to define an internal volume. The bridge sealing member may include a substantially liquid impermeable and vapor permeable film. Further, the bridge sealing member may define an internal passageway in fluid communication between the receiving end and the transmitting end. The first bridge wicking layer and the second bridge wicking layer may be disposed within the internal passageway.

In some embodiments, the bridge may alternatively or additionally a bridge absorbent disposed within the internal volume between the first bridge wicking layer and the second bridge wicking layer. The fluid distribution surface of the first bridge wicking layer and the second bridge wicking layer may face the bridge absorbent. At least a portion of the bridge absorbent may be spaced apart from the fluid distribution surface of the first bridge wicking layer and the second bridge wicking layer. The fluid distribution surface of the first bridge wicking layer and the second bridge wicking layer may include a plurality of longitudinal fibers oriented substantially in a longitudinal direction along the length. The fluid acquisition surface of the first bridge wicking layer and the second bridge wicking layer may include a plurality of vertical fibers oriented substantially normal relative to the longitudinal fibers.

Other aspects, features, and advantages of the illustrative examples will become apparent with reference to the drawings and detailed description that follow.

BRIEF DESCRIPTION OF THE DRAWINGS

FIG. 9 is a plan view of an illustrative example of a bridge assembly suitable for use with the system and the dressing of FIG. 1;

FIG. 10 is a cross-section of an illustrative example of a storage bridge shown with the bridge assembly of FIG. 9, taken at lines 10-10;

FIG. 14 is a cut-away view of the dressing of FIG. 13;

FIG. 15 is a detail view taken at reference FIG. 15, shown in FIG. 13, illustrating the dressing of FIG. 13 positioned proximate to tissue surrounding the tissue site;

DETAILED DESCRIPTION OF ILLUSTRATIVE EMBODIMENTS

In the following detailed description of illustrative example embodiments, reference is made to the accompanying drawings that form a part of this disclosure. Other embodiments may be used, and logical, structural, mechanical, electrical, and chemical changes may be made without departing from the scope of this disclosure. Further, the description may omit certain information known to those skilled in the art. Therefore, the following detailed description is non-limiting, and the appended claims define the scope of the illustrative embodiments. Further, as used throughout this disclosure, "or" does not require mutual exclusivity.

Figure 1:
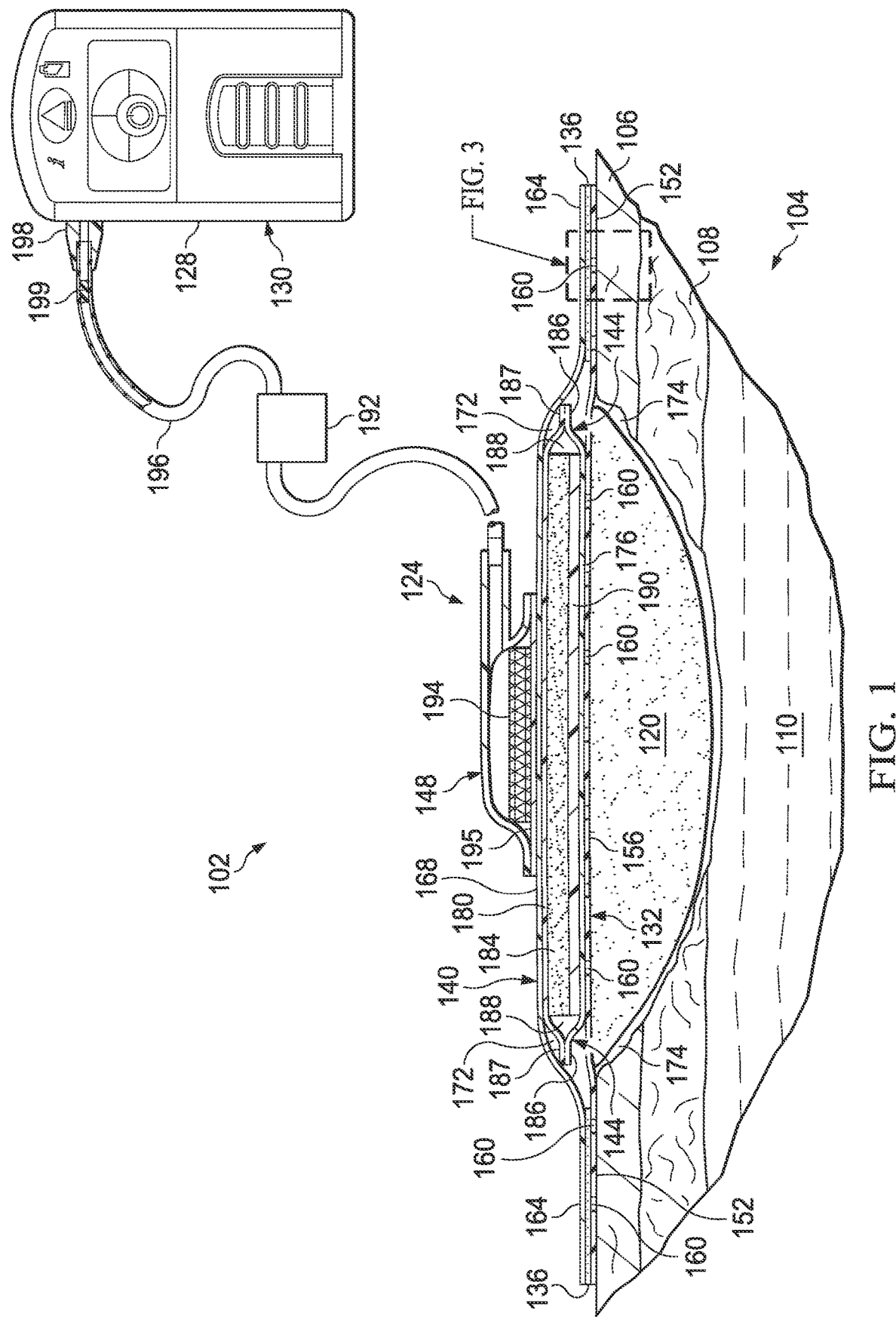
FIG. 1 is a cut-away view of an illustrative example of a system for treating a tissue site depicting an illustrative example of a dressing deployed at the tissue site.

Referring to the drawings, FIG. 1 depicts an illustrative embodiment of a system 102 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that may extend below the surface of the epidermis 106. Further, the tissue site 104 may be a surface tissue site (not shown) that may predominantly reside on the surface of the epidermis 106, such as, for example, an incision. The system 102 may provide therapy to, for example, the epidermis 106, the dermis 108, and the subcutaneous tissue 110, regardless of the positioning of the system 102 or the type of tissue site. The system 102 may also be used without limitation at other tissue sites.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 104 may include the removal of fluids, such as exudate or ascites.

Continuing with FIG. 1, the system 102 may include an optional tissue interface, such as an interface manifold 120. Further, the system 102 may include a dressing 124 and a reduced-pressure source 128. The reduced-pressure source 128 may be a component of an optional therapy unit 130. In some embodiments, the reduced-pressure source 128 and the therapy unit 130 may be separate components. Further, in some embodiments, the interface manifold 120 may be omitted for different types of tissue sites or different types of therapy, such as, for example, epithelialization. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104. In some embodiments, the interface manifold 120 may be positioned in direct contact with the tissue site 104.

The tissue interface or the interface manifold 120 may be formed from any manifold material or flexible bolster material that provides a vacuum space, or treatment space, such as, for example, a porous and permeable foam or foam-like material, a member formed with pathways, a graft, or a gauze. In some embodiments, the interface manifold 120 may be a reticulated, open-cell polyurethane or polyether foam that may be fluid permeable while under a reduced pressure. One such foam material is VAC® GranuFoam® material available from Kinetic Concepts, Inc. (KCI) of San Antonio, Texas. Further, in some embodiments, any material or combination of materials may be used as a manifold material for the interface manifold 120 provided that the manifold material is operable to distribute or collect fluid. For example, herein the term manifold may refer to a substance or structure configured for delivering fluids to or removing fluids from a tissue site through a plurality of pores, pathways, or flow channels. The plurality of pores, pathways, or flow channels may be interconnected to improve the distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, a material with a higher or lower density than GranuFoam® material may be desirable for the interface manifold 120 depending on the application. Among the many possible materials, the following may be used without limitation: GranuFoam® material; Foamex® technical foam (www.foamex.com); a molded bed of nails structure; a patterned grid material, such as those manufactured by Sercol Industrial Fabrics; 3D textiles, such as those manufactured by Baltex of Derby, U.K.; a gauze; a flexible channel-containing member; or a graft. Further, in some embodiments, ionic silver may be added to the interface manifold 120 by, for example, a micro bonding process. Other substances, such as anti-microbial agents, may be added to the interface manifold 120 as well.

In some embodiments, the interface manifold 120 may comprise a porous, hydrophobic material. The hydrophobic characteristics of the interface manifold 120 may prevent the interface manifold 120 from directly absorbing fluid, such as exudate, from the tissue site 104, but allow the fluid to pass through.

In some embodiments, the dressing 124 may include a base layer 132, an adhesive 136, a sealing member 140, a fluid management assembly 144, and a conduit interface 148. Components of the dressing 124 may be added or removed to suit a particular application. In some embodiments, the dressing 124 may be adapted to provide reduced pressure from the reduced-pressure source 128 to the interface manifold 120, and to extract fluid from the tissue site 104 through the interface manifold 120.

Referring to FIGS. 1-4B, the base layer 132 may have a periphery 152 surrounding a central portion 156, and a plurality of apertures 160 disposed through the periphery 152 and the central portion 156. The base layer 132 may also have corners 158 and edges 159. The corners 158 and the edges 159 may be part of the periphery 152. One of the edges 159 may meet another of the edges 159 to define one of the corners 158. Further, the base layer 132 may have a border 161 substantially surrounding the central portion 156 and positioned between the central portion 156 and the periphery 152. In some embodiments, the border 161 may be free of the apertures 160. In some embodiments, the base layer 132 may be adapted to cover the interface manifold 120 and tissue surrounding the tissue site 104 such that the central portion 156 of the base layer 132 is positioned adjacent to or proximate to the interface manifold 120, and the periphery 152 of the base layer 132 is positioned adjacent to or proximate to tissue surrounding the tissue site 104. In such embodiments, the periphery 152 of the base layer 132 may surround the interface manifold 120. Further, the apertures 160 in the base layer 132 may be in fluid communication with the interface manifold 120 and tissue surrounding the tissue site 104.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. Each of the apertures 160 of the plurality of apertures 160 may be substantially circular in shape, having a diameter and an area. The area of the apertures 160 described in the illustrative embodiments herein may be substantially similar to the area in other embodiments for the apertures 160 that may have non-circular shapes. Further, the area of each of the apertures 160 may be substantially the same, or each of the areas may vary, for example, based on the position of the aperture 160 in the base layer 132. For example, the area of the apertures 160 in the periphery 152 of the base layer 132 may be larger than the area of the apertures 160 in the central portion 156 of the base layer 132. The apertures 160 may have a uniform pattern or may be randomly distributed on the base layer 132. The size and configuration of the apertures 160 may be designed to control the adherence of the dressing 124 to the epidermis 106 as described below.

In some embodiments, the apertures 160 positioned in the periphery 152 may be apertures 160a, the apertures 160 positioned at the corners 158 of the periphery 152 may be apertures 160b, and the apertures 160 positioned in the central portion 156 may be apertures 160c. In some embodiments, the apertures 160a may have an area greater than the apertures 160b. Further, in some embodiments, the apertures 160b may have an area greater than the apertures 160c. The dimensions of the base layer 132 may be increased or decreased, for example, substantially in proportion to one another to suit a particular application. Further, although the central portion 156, the border 161, and the periphery 152 of the base layer 132 are shown as having a substantially square shape, these and other components of the base layer 132 may have any shape to suit a particular application.

The base layer 132 may be a soft, pliable material suitable for providing a fluid seal with the tissue site 104 as described herein. For example, the base layer 132 may comprise a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive as described below, polyurethane, polyolefin, or hydrogenated styrenic copolymers. In some embodiments, the base layer 132 may include a silicone such as Scapa Soft-Pro®. The base layer 132 may have a thickness between about 500 microns (μm) and about 1000 microns (μm). In some embodiments, the base layer 132 may have a stiffness between about 5 Shore OO and about 80 Shore OO. Further, in some embodiments, the base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the adhesive 136 may extend through openings in the spaced material analogous to the apertures 160.

In some embodiments, the adhesive 136 may be exposed to the apertures 160 in at least the periphery 152 of the base layer 132. Further, in some embodiments, the adhesive 136 may be positioned adjacent to, or positioned in fluid communication with, the apertures 160 in at least the periphery 152 of the base layer 132. Further, in some embodiments, the adhesive 136 may be exposed to or in fluid communication with tissue surrounding the tissue site 104 through the apertures 160 in the base layer 132. As described further below and shown in FIG. 3, the adhesive 136 may extend, deform, or be pressed through the plurality of apertures 160 to contact the epidermis 106 for securing the dressing 124 to, for example, tissue surrounding the tissue site 104. The apertures 160 may provide sufficient contact of the adhesive 136 to the epidermis 106 to secure the dressing 124 about the tissue site 104. However, the configuration of the apertures 160 and the adhesive 136, described below, may permit release and repositioning of the dressing 124 about the tissue site 104.

In some embodiments, the apertures 160b at the corners 158 of the periphery 152 may be smaller than the apertures 160a in other portions of the periphery 152. For a given geometry of the corners 158, the smaller size of the apertures 160b compared to the apertures 160a may enhance or increase the surface area of the adhesive 136 exposed to the apertures 160b and to tissue through the apertures 160b at the corners 158. The size and number of the apertures 160b in the corners 158 may be adjusted as necessary, depending on the chosen geometry of the corners 158, to enhance or increase the exposed surface area of the adhesive 136 as described above.

Similar to the apertures 160b in the corners 158, any of the apertures 160 may be adjusted in size and number to increase the surface area of the adhesive 136 exposed to or in fluid communication with the apertures 160 for a particular application or geometry of the base layer 132. For example, in some embodiments (not shown) the apertures 160b, or apertures of another size, may be positioned in the periphery 152 and at the border 161. Similarly, the apertures 160b, or apertures of another size, may be positioned as described above in other locations of the base layer 132 that may have a complex geometry or shape.

The adhesive 136 may be a medically-acceptable adhesive. In some embodiments, the adhesive 136 may be deformable or flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive. The adhesive 136 may be a layer having substantially the same shape as the periphery 152 of the base layer 132. In some embodiments, the adhesive 136 may be continuous or discontinuous. Discontinuities in the adhesive 136 may be provided by apertures (not shown) in the adhesive 136. Apertures in the adhesive 136 may be formed after application of the adhesive 136 or by coating the adhesive 136 in patterns on a carrier layer, such as, for example, a side of the sealing member 140 adapted to face the epidermis 106.

Further, apertures in the adhesive 136 may be sized to control the amount of the adhesive 136 extending through the apertures 160 in the base layer 132 to reach the epidermis 106. Apertures in the adhesive 136 may also be sized to enhance the Moisture Vapor Transfer Rate (MVTR) of the dressing 124, described further below.

Factors that may be utilized to control the adhesion strength of the dressing 124 may include the diameter, area, and number of the apertures 160 in the base layer 132, the thickness of the base layer 132, the thickness and amount of the adhesive 136, and the tackiness of the adhesive 136. An increase in the amount of the adhesive 136 extending through the apertures 160 may correspond to an increase in the adhesion strength of the dressing 124. A decrease in the thickness of the base layer 132 may correspond to an increase in the amount of adhesive 136 extending through the apertures 160. Thus, the diameter, area, and configuration of the apertures 160, the thickness of the base layer 132, and the amount and tackiness of the adhesive utilized may be varied to provide a desired adhesion strength for the dressing 124.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b and 160c. In this manner, locations of the base layer 132 having larger apertures 160 and lower tackiness adhesive 136 may have an adhesion strength comparable to locations having smaller apertures 160 and higher tackiness adhesive 136.

A release liner 162 may be attached to or positioned adjacent to the base layer 132 to protect the adhesive 136 prior to application of the dressing 124 to the tissue site 104. Prior to application of the dressing 124 to the tissue site 104, the base layer 132 may be positioned between the sealing member 140 and the release liner 162. Removal of the release liner 162 may expose the base layer 132 and the adhesive 136 for application of the dressing 124 to the tissue site 104. The release liner 162 may also provide stiffness to assist with, for example, deployment of the dressing 124. The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 124. For example, the polar semi-crystalline polymer may be highly orientated and resistant to softening, swelling, or other deformation that may occur when brought into contact with components of the dressing 124, or when subjected to temperature or environmental variations, or sterilization. Further, a release agent may be disposed on a side of the release liner 162 that is configured to contact the base layer 132. For example, the release agent may be a silicone coating and may have a release factor suitable to facilitate removal of the release liner 162 by hand and without damaging or deforming the dressing 124. In some embodiments, the release agent may be fluorosilicone. In other embodiments, the release liner 162 may be uncoated or otherwise used without a release agent.

Continuing with FIGS. 1-4B, the sealing member 140 may also be referred to as a dressing sealing member 140. The sealing member 140 may have a periphery 164 and a central portion 168. The sealing member 140 may additionally include an aperture 170. The periphery 164 of the sealing member 140 may be positioned proximate to the periphery 152 of the base layer 132 such that the central portion 168 of the sealing member 140 and the central portion 156 of the base layer 132 define an enclosure 172. The adhesive 136 may be positioned at least between the periphery 164 of the sealing member 140 and the periphery 152 of the base layer 132. The sealing member 140 may cover the tissue site 104 and the interface manifold 120 to provide a fluid seal and a sealed space 174 between the tissue site 104 and the sealing member 140 of the dressing 124. Further, the sealing member 140 may cover other tissue, such as a portion of the epidermis 106, surrounding the tissue site 104 to provide the fluid seal between the sealing member 140 and the tissue site 104. In some embodiments, a portion of the periphery 164 of the sealing member 140 may extend beyond the periphery 152 of the base layer 132 and into direct contact with tissue surrounding the tissue site 104. In other embodiments, the periphery 164 of the sealing member 140, for example, may be positioned in contact with tissue surrounding the tissue site 104 to provide the sealed space 174 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal may be a seal adequate to maintain reduced pressure at a desired site given the particular reduced pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, California; a polyurethane (PU) film such as Scapa Bioflex 130 polyurethane Film®; polyether block polyamide copolymer (PEBAX), for example, from Arkema, France; Expopack 2327; or other appropriate material.

The sealing member 140 may be vapor permeable and liquid impermeable, thereby allowing vapor and inhibiting liquids from exiting the sealed space 174 provided by the dressing 124. In some embodiments, the sealing member 140 may be a flexible, breathable film, membrane, or sheet having a high MVTR of, for example, at least about 300 g/m² per 24 hours.

In other embodiments, a low or no vapor transfer drape may be used. The sealing member 140 may comprise a range of medically suitable films having a thickness between about 15 microns (μm) to about 50 microns (μm).

The fluid management assembly 144 may be disposed in the enclosure 172. In some embodiments, the fluid management assembly 144 may include a first dressing wicking layer 176, a second dressing wicking layer 180, and an absorbent layer 184. The absorbent layer 184 may also be referred to as a dressing absorbent 184. The absorbent layer 184 may be positioned in fluid communication between the first dressing wicking layer 176 and the second dressing wicking layer 180. The first dressing wicking layer 176 may have a grain structure adapted to wick fluid along a surface of the first dressing wicking layer 176. Similarly, the second dressing wicking layer 180 may have a grain structure adapted to wick fluid along a surface of the second dressing wicking layer 180. For example, the first dressing wicking layer 176 and the second dressing wicking layer 180 may wick or otherwise transport fluid in a lateral direction along the surfaces of the first dressing wicking layer 176 and the second dressing wicking layer 180, respectively. The surface of the first dressing wicking layer 176 may be normal relative to the thickness of the first dressing wicking layer 176, and the surface of the second dressing wicking layer 180 may be normal relative to the thickness of the second dressing wicking layer 180. The wicking of fluid along the first dressing wicking layer 176 and the second dressing wicking layer 180 may enhance the distribution of the fluid over a surface area of the absorbent layer 184, which may increase absorbent efficiency and resist fluid blockages. Fluid blockages may be caused by, for example, fluid pooling in a particular location in the absorbent layer 184 rather than being distributed more uniformly across the absorbent layer 184. The laminate combination of the first dressing wicking layer 176, the second dressing wicking layer 180, and the absorbent layer 184 may be adapted as described above to maintain an open structure, resistant to blockage, capable of maintaining fluid communication with, for example, the tissue site 104.

Referring to the embodiments of the fluid management assembly 144 depicted in FIGS. 1, 2, 5, and 6, a peripheral portion 186 of the first dressing wicking layer 176 may be coupled to a peripheral portion 187 of the second dressing wicking layer 180 to define a wicking layer enclosure 188 between the first dressing wicking layer 176 and the second dressing wicking layer 180. In some embodiments, the wicking layer enclosure 188 may surround or otherwise encapsulate the absorbent layer 184 between the first dressing wicking layer 176 and the second dressing wicking layer 180.

Figure 5:
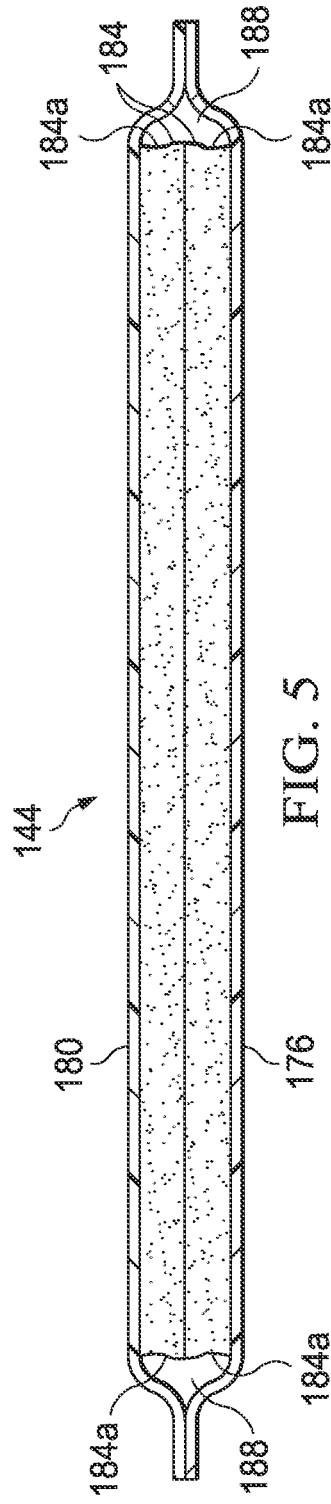
FIG. 5 is a cut-away view of an illustrative example of a fluid management assembly suitable for use with the dressing and system of FIG. 1.
Figure 6:
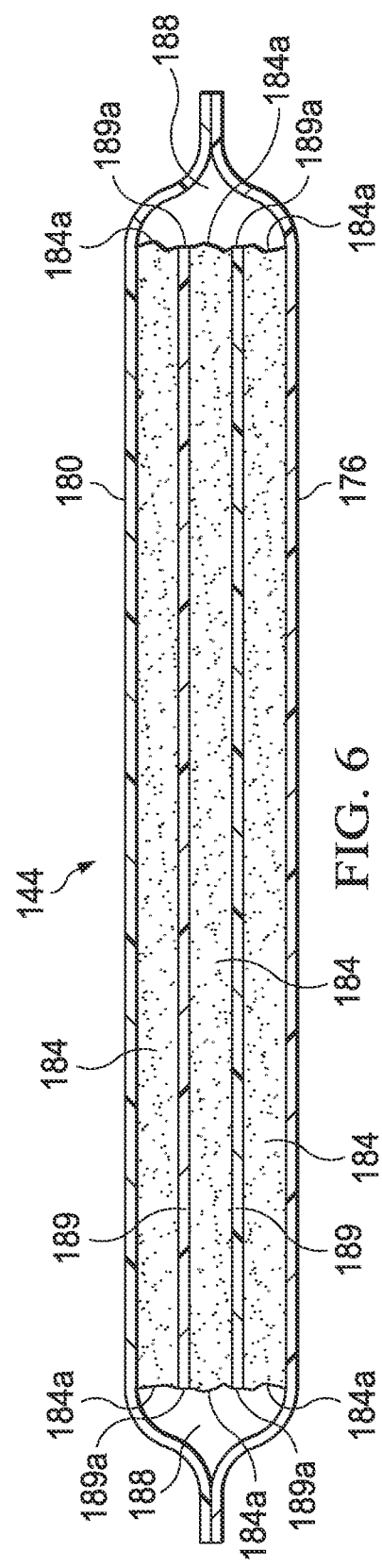
FIG. 6 is a cut-away view of another illustrative example of a fluid management assembly suitable for use with the dressing and system of FIG. 1.

Referring to FIGS. 5 and 6, in some embodiments, the fluid management assembly 144 may include, without limitation, any number of wicking layers and absorbent layers as desired for treating a particular tissue site. For example, the absorbent layer 184 may be a plurality of absorbent layers 184 positioned in fluid communication between the first dressing wicking layer 176 and the second dressing wicking layer 180. Further, as shown in FIG. 6, in some embodiments, at least one intermediate wicking layer 189 may be disposed in fluid communication between the plurality of absorbent layers 184. Similar to the absorbent layer 184, the plurality of absorbent layers 184 and the at least one intermediate wicking layer 189 may be positioned within the wicking layer enclosure 188. In some embodiments, the absorbent layer 184 may be disposed between the sealing member 140 and the interface manifold 120, and the first dressing wicking layer 176 and the second dressing wicking layer 180 may be omitted.

Continuing with FIGS. 5 and 6, sides 184a of the absorbent layers 184 may remain in fluid communication with one another for enhancing efficiency. Similarly, sides 189a of the at least one intermediate wicking layer 189 shown in FIG. 6 may remain in fluid communication with one another and with the sides 184a of the absorbent layers 184. Further, including additional absorbent layers 184 may increase the absorbent mass of the fluid management assembly 144 and generally provide greater fluid capacity. However, for a given absorbent mass, multiple light coat-weight absorbent layers 184 may be utilized rather than a single heavy coat-weight absorbent layer 184 to provide a greater absorbent surface area for further enhancing the absorbent efficiency.

In some embodiments, the absorbent layer 184 may be a hydrophilic material adapted to absorb fluid from, for example, the tissue site 104. Materials suitable for the absorbent layer 184 may include, without limitation, super absorbent polymers and similar absorbent materials; Luquafleece® material; TEXSUS FP2326; BASF 402C; Technical Absorbents 2317, available from Technical Absorbents, Ltd. of Lincolnshire, United Kingdom; sodium polyacrylate super absorbers; cellulosics (carboxy methyl cellulose and salts such as sodium CMC); Gelok® 30040-76 S/S/S 300 gsm absorbent; or alginates. Materials suitable for the first dressing wicking layer 176 and the second dressing wicking layer 180 may include, without limitation, any material having a grain structure capable of wicking fluid as described herein, such as, for example, LIBELTEX TDL2, 80 gsm, or similar materials, which may be non-woven.

The fluid management assembly 144 may be manufactured as a pre-laminated structure, or supplied as individual layers of material that can be stacked upon one another as described above. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161, being free of the apertures 160 as described above, may provide a flexible barrier between the fluid management assembly 144 and the tissue site 104 for enhancing comfort.

The dressing 124 may be modified in various embodiments to suit a particular application. In some embodiments, the absorbent layer 184 may be omitted from the fluid management assembly 144, which may be beneficial, but not required, for communicating fluid exterior to or away from the dressing 124 and the tissue site 104 for offsite or remote storage. In such an embodiment, the first dressing wicking layer 176 and the second dressing wicking layer 180 may wick or draw fluid away from the tissue site 104 for transport to a location exterior to the dressing 124. Further, the configuration of the first dressing wicking layer 176 and the second dressing wicking layer 180 described herein may preference fluid away from the tissue site 104 and prevent the fluid from returning to the tissue site 104 prior to removal of the fluid from the dressing 124, for example, by the application of reduced pressure. The wicking layer enclosure 188 may enhance this ability to preference fluid away from the tissue site 104 and to prevent the fluid from returning to the tissue site 104.

The dressing 124 may be further modified in various embodiments that may be suitable for some applications that communicate fluid from the tissue site 104 exterior to the dressing 124. For example, in some embodiments, the first dressing wicking layer 176 or the second dressing wicking layer 180 may be omitted along with the absorbent layer 184 and the base layer 132. In such an embodiment, the dressing 124 may comprise the sealing member 140 and one of the first dressing wicking layer 176 or the second dressing wicking layer 180 for disposing in the sealed space 174 between the sealing member 140 and the tissue site 104.

Further, in some embodiments, the fluid management assembly 144 may be omitted from the dressing 124, and a dressing manifold (not shown) may be positioned in the enclosure 172 in place of the fluid management assembly 144. The dressing manifold may be configured as a layer and may be comprised of any material suitable for removing fluids from a tissue site through a plurality of pores, pathways, or flow channels as described herein, such as, without limitation, a foam, a woven material, a cast silicone, a polyurethane material, or any of the materials recited above for the interface manifold 120. Further, in some embodiments, the dressing 124 may be modified by omitting the base layer 132 and replacing the fluid management assembly 144 with the above-described dressing manifold. In such an embodiment, the dressing 124 may comprise the sealing member 140 and the dressing manifold for disposing in the sealed space 174 between the sealing member 140 and the tissue site 104. Further, in some embodiments, the absorbent layer 184 may be omitted and replaced with the dressing manifold such that the dressing manifold is positioned between the first dressing wicking layer 176 and the second dressing wicking layer 180.

Figure 2:
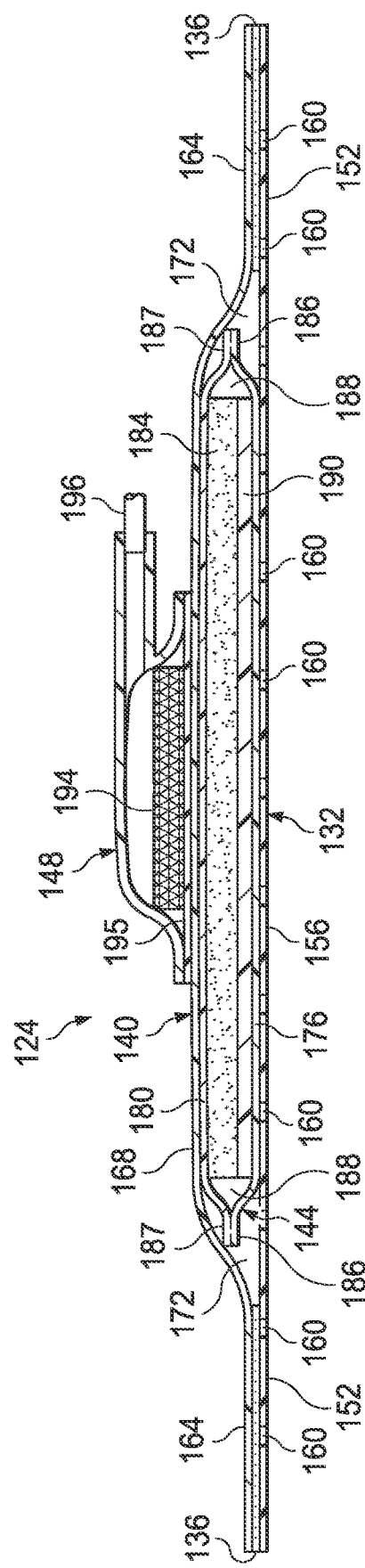
FIG. 2 is a cut-away view of the dressing of FIG. 1.
Figure 3:
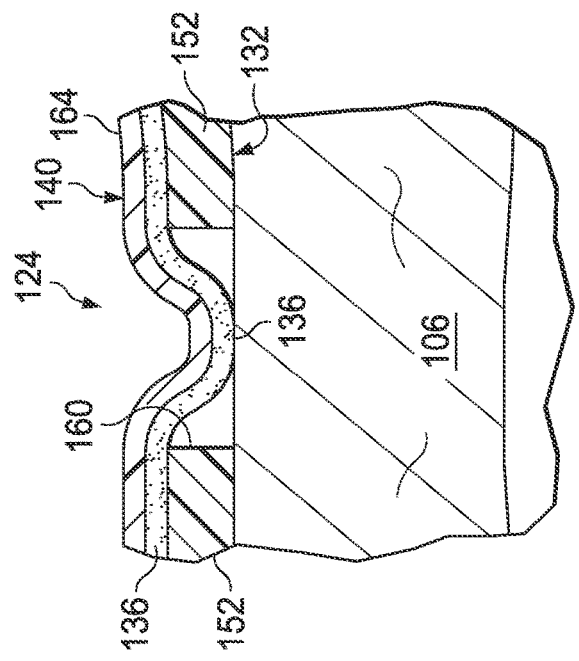
FIG. 3 is detail view taken at reference FIG. 3, shown in FIG. 1, illustrating the dressing of FIG. 1 positioned proximate to tissue surrounding the tissue site.
Figure 4A:
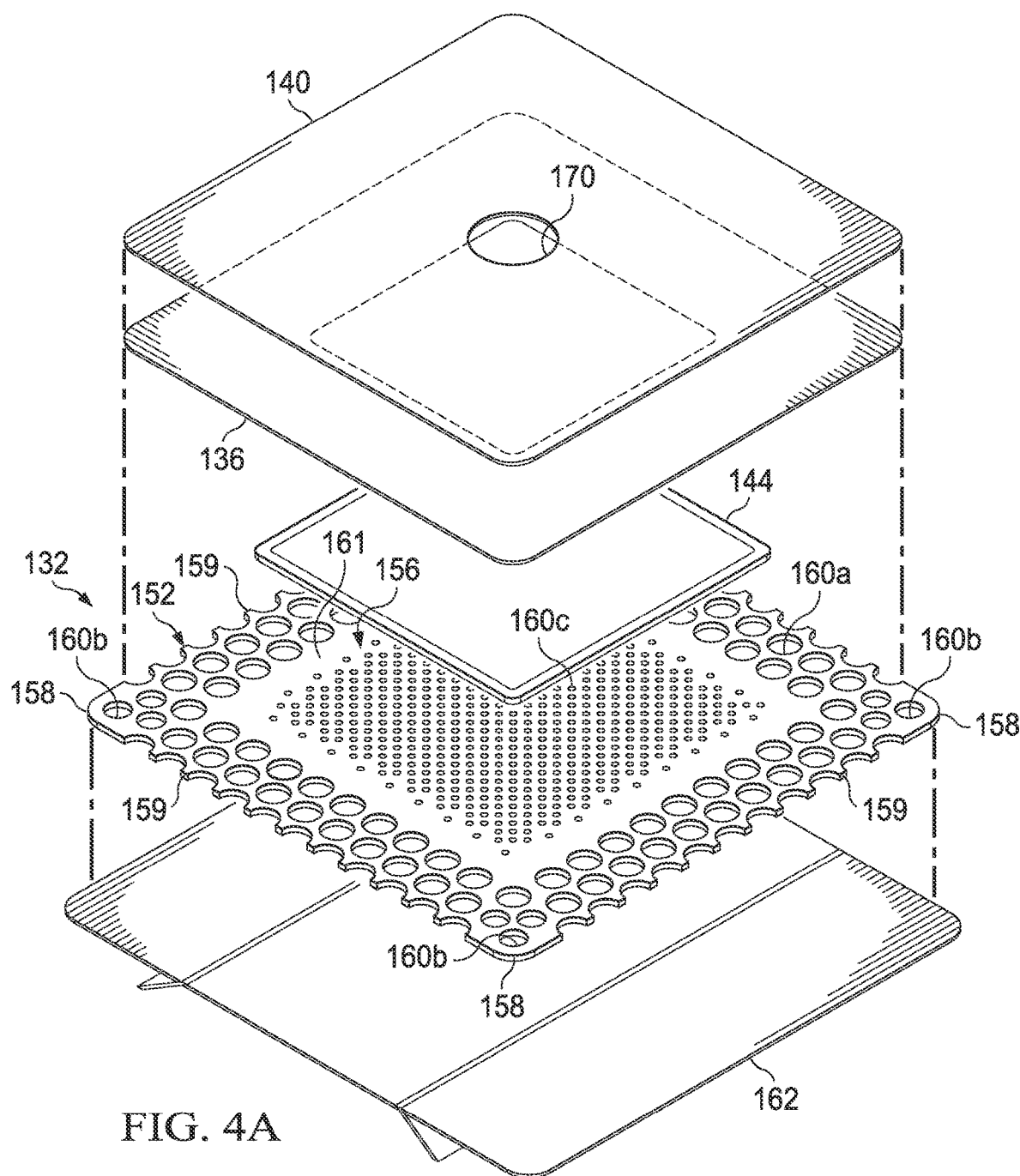
FIG. 4A is an exploded view of the dressing of FIG. 1, depicted without a conduit interface and with an illustrative example of a release liner for protecting the dressing prior to application at the tissue site.
Figure 4B:
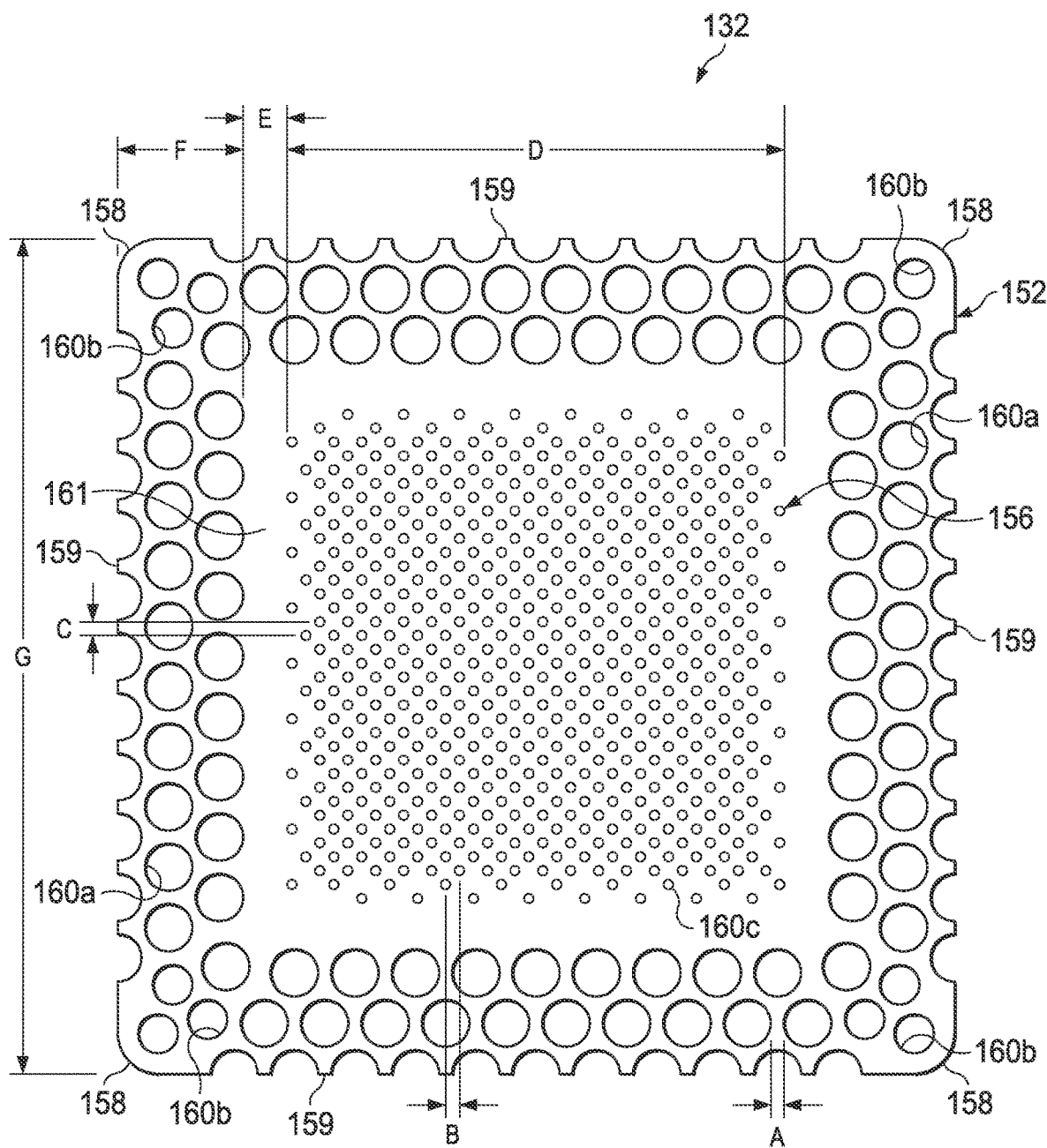
FIG. 4B is a plan view of an illustrative example of a base layer depicted in the dressing of FIG. 4A.

Referring to FIGS. 1 and 2, in some embodiments, the enclosure 172 defined by the base layer 132 and the sealing member 140 may include an optional anti-microbial layer 190. The addition of the anti-microbial layer 190 may reduce the probability of excessive bacterial growth within the dressing 124 to permit the dressing 124 to remain in place for an extended period. The anti-microbial layer 190 may be, for example, an additional layer included as a part of the fluid management assembly 144, or a coating of an anti-microbial agent disposed in any suitable location within the dressing 124. The anti-microbial layer 190 may be comprised of elemental silver or a similar compound, for example. In some embodiments, the anti-microbial agent may be formulated in any suitable manner and associated with other components of the dressing 124.

Figure 7:
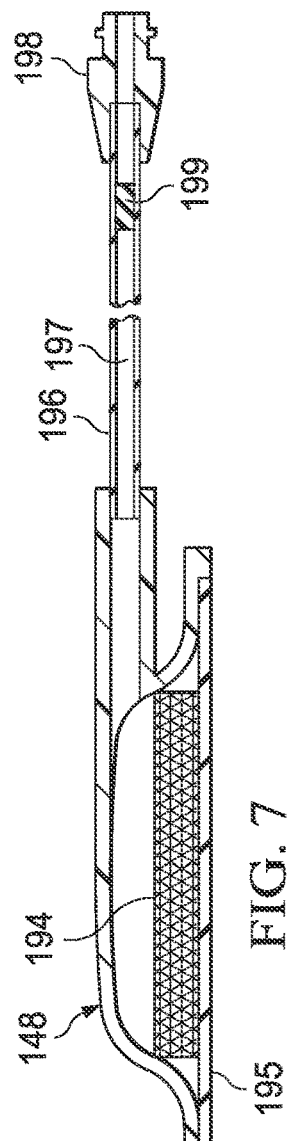
FIG. 7 is a cut-away view of an illustrative example of a conduit interface shown with the dressing of FIG. 1.

Referring to FIGS. 1, 2, and 7, the conduit interface 148 may be positioned proximate to the sealing member 140 and in fluid communication with the enclosure 172 of the dressing 124. For example, the conduit interface 148 may be in fluid communication with the dressing 124 through the aperture 170 in the sealing member 140. The conduit interface 148 may provide reduced pressure from the reduced-pressure source 128 to the dressing 124. The conduit interface 148 may also be adapted to be positioned in fluid communication with the optional interface manifold 120. An optional liquid trap 192 may be positioned in fluid communication between the dressing 124 and the reduced-pressure source 128. The liquid trap 192 may be any suitable containment device having a sealed internal volume capable of retaining liquid, such as condensate or other liquids.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene. In some illustrative, non-limiting embodiments, conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the dressing 124 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 102. Further, the absorbent material or hydrophilic polymer may be suitable for use in various components of the system 102 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 102, relative to the temperature at the tissue site 104. Removal or dissipation of liquids from the conduit interface 148 may increase visual appeal and prevent odor. Further, such removal of liquids may also increase efficiency and reliability by reducing blockages and other interference with the components of the system 102.

Similar to the conduit interface 148, the liquid trap 192, and other components of the system 102, may also be formed of an absorbent material or a hydrophilic polymer. The absorptive and evaporative properties of the hydrophilic polymer may also facilitate removal and dissipation of liquids residing in the liquid trap 192, and other components of the system 102, by evaporation. Such evaporation may leave behind a substantially solid or gel-like waste. The substantially solid or gel-like waste may be cheaper to dispose than liquids, providing a cost savings for operation of the system 102. The hydrophilic polymer may be used for other components in the system 102 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 102 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 102. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

The conduit interface 148 may carry an odor filter 194 adapted to substantially preclude the passage of odors from the tissue site 104 out of the sealed space 174. Further, the conduit interface 148 may carry a primary hydrophobic filter 195 adapted to substantially preclude the passage of liquids through the primary hydrophobic filter 195. The odor filter 194 and the primary hydrophobic filter 195 may be disposed in the conduit interface 148 or other suitable location such that fluid communication between the reduced-pressure source 128, or optional therapy unit 130, and the dressing 124 is provided through the odor filter 194 and the primary hydrophobic filter 195. In some embodiments, the odor filter 194 and the primary hydrophobic filter 195 may be secured within the conduit interface 148 in any suitable manner, such as by adhesive or welding. In other embodiments, the odor filter 194 or the primary hydrophobic filter 195 may be omitted, or positioned proximate to any exit location in the system 102 or the dressing 124 that is in fluid communication with the atmosphere, the reduced-pressure source 128, or the optional therapy unit 130.

The odor filter 194 may be comprised of a carbon material in the form of a layer or particulate. For example, the odor filter 194 may comprise a woven carbon cloth filter such as those manufactured by Chemviron Carbon, Ltd. of Lancashire, United Kingdom. The primary hydrophobic filter 195 may be comprised of a material that is liquid impermeable and vapor permeable. For example, the primary hydrophobic filter 195 may comprise a material manufactured under the designation MMT-314 by W.L. Gore & Associates, Inc. of Newark, Delaware, United States, or similar materials. The primary hydrophobic filter 195 may be provided in the form of a membrane or layer.

Continuing with FIGS. 1, 2, and 7, the reduced-pressure source 128 may provide reduced pressure to the dressing 124 and the sealed space 174. The reduced-pressure source 128 may be any suitable device for providing reduced pressure, such as, for example, a vacuum pump, wall suction, hand pump, manual pump, or other source. In some embodiments, the reduced-pressure source 128 may be a component of the therapy unit 130. The therapy unit 130 may include control circuitry and sensors, such as a pressure sensor, that may be configured to monitor reduced pressure at the tissue site 104. The therapy unit 130 may also be configured to control the amount of reduced pressure from the reduced-pressure source 128 being applied to the tissue site 104 according to a user input and a reduced-pressure feedback signal received from the tissue site 104. In some embodiments, the reduced pressure source 128 (such as a manual pump, hand pump, or the like) may comprise a container or may be fluidly connected to a container that receives fluid collected from the tissue site 104. Thus, when the reduced pressure source 128 generates reduced pressure, fluid may be communicated from the tissue site, through the dressing, through the bridge, and received and stored in the container of the reduced pressure source 128 or fluidly connected to the reduced pressure source 128.

As used herein, "reduced pressure" may refer to a pressure less than the ambient pressure at a tissue site being subjected to treatment. In some embodiments, the reduced pressure may be less than the atmospheric pressure. Further, in some embodiments, the reduced pressure may also be less than a hydrostatic pressure at a tissue site. Unless otherwise indicated, values of pressure stated herein are gauge pressures. While the amount and nature of reduced pressure applied to a tissue site may vary according to the application, in some embodiments, the reduced pressure may be between −5 mm Hg and −500 mm Hg. In some embodiments, the reduced pressure may be between −100 mm Hg and −200 mm Hg.

The reduced pressure delivered may be, for example, constant, varied, patterned, or random. Further, the reduced pressure may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refer to a relative reduction in absolute pressure. Further, an increase in reduced pressure may correspond to a reduction in pressure (more negative relative to ambient pressure), and a decrease in reduced pressure may correspond to an increase in pressure (less negative relative to ambient pressure).

Referring to FIGS. 1 and 7, a conduit 196 having an internal lumen 197 may be coupled in fluid communication between the reduced-pressure source 128 and the dressing 124. The internal lumen 197 may have an internal diameter between about 0.5 millimeters to about 3.0 millimeters. In some embodiments, the internal diameter of the internal lumen 197 may be between about 1 millimeter to about 2 millimeters. The conduit interface 148 may be coupled in fluid communication with the dressing 124 and adapted to connect between the conduit 196 and the dressing 124 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The aperture 170 in the sealing member 140 may provide fluid communication between the dressing 124 and the conduit interface 148. For example, the conduit interface 148 may be in fluid communication with the enclosure 172 or the sealed space 174 through the aperture 170 in the sealing member 140. In some embodiments, the conduit 196 may be inserted into the dressing 124 through the aperture 170 in the sealing member 140 to provide fluid communication with the reduced-pressure source 128 without use of the conduit interface 148. The reduced-pressure source 128 may also be directly coupled in fluid communication with the dressing 124 or the sealing member 140 without use of the conduit 196. In some embodiments, the conduit 196 may be, for example, a flexible polymer tube. A distal end of the conduit 196 may include a coupling 198 for attachment to the reduced-pressure source 128.

The conduit 196 may have a secondary hydrophobic filter 199 disposed in the internal lumen 197 such that fluid communication between the reduced-pressure source 128 and the dressing 124 is provided through the secondary hydrophobic filter 199. The secondary hydrophobic filter 199 may be, for example, a porous, sintered polymer cylinder sized to fit the dimensions of the internal lumen 197 to substantially preclude liquid from bypassing the cylinder. The secondary hydrophobic filter 199 may also be treated with an absorbent material adapted to swell when brought into contact with liquid to block the flow of the liquid. The secondary hydrophobic filter 199 may be positioned at any location within the internal lumen 197. However, positioning the secondary hydrophobic filter 199 within the internal lumen 197 closer toward the reduced-pressure source 128, rather than the dressing 124, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application.

Figure 8:
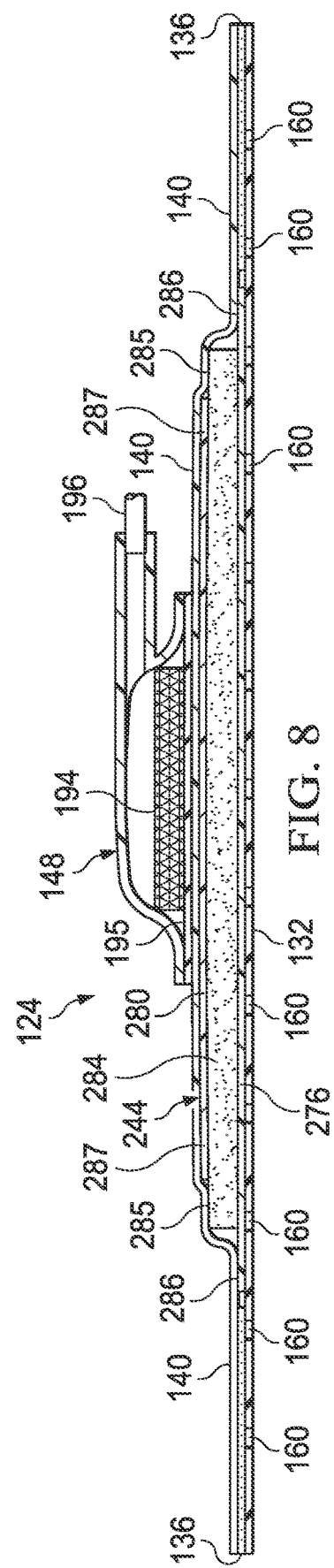
FIG. 8 is a cut-away view of another illustrative example of a dressing and a fluid management assembly suitable for use with the system of FIG. 1.

Referring to FIG. 8, another embodiment of a fluid management assembly 244 suitable for use with the dressing 124 and the system 102 is shown. The fluid management assembly 244 may include a first dressing wicking layer 276, a second dressing wicking layer 280, and an absorbent layer 284 comprised of substantially the same materials and properties as those described above in connection with the fluid management assembly 144. Thus, the first dressing wicking layer 276, the second dressing wicking layer 280, and the absorbent layer 284 may be analogous to the first dressing wicking layer 176, the second dressing wicking layer 180, and the absorbent layer 184, respectively.

In the fluid management assembly 244, the second dressing wicking layer 280 may have a peripheral portion 287. The second dressing wicking layer 280 and the peripheral portion 287 of the second dressing wicking layer 280 may be positioned in contact with the sealing member 140. The absorbent layer 284 may have a peripheral portion 285 extending beyond the peripheral portion 287 of the second dressing wicking layer 280. The absorbent layer 284 may be positioned adjacent to or proximate to the second dressing wicking layer 280 such that the peripheral portion 285 of the absorbent layer 284 is in contact with the sealing member 140 surrounding the peripheral portion 287 of the second dressing wicking layer 280. Similarly, the first dressing wicking layer 276 may have a peripheral portion 286 extending beyond the peripheral portion 285 of the absorbent layer 284. The first dressing wicking layer 276 may be positioned adjacent to or proximate to the absorbent layer 284 such that the peripheral portion 286 of the first dressing wicking layer 276 is in contact with the sealing member 140 surrounding the peripheral portion 285 of the absorbent layer 284. Further, the first dressing wicking layer 276 may be positioned adjacent to or proximate to the base layer 132. Thus, at least the peripheral portion 287, the peripheral portion 285, and the peripheral portion 286 may be coupled to the sealing member 140, such as, for example, by an adhesive coating disposed on a surface of the sealing member 140 facing the base layer 132. The adhesive coating may be analogous to the adhesive 136 that may be applied across the surface of the sealing member 140 facing the base layer 132. The second dressing wicking layer 280, the absorbent layer 284, and the first dressing wicking layer 276 may respectively have increasing surface areas to enhance contact with the adhesive coating described above. In other embodiments, the fluid management assembly 244 may include any number of absorbent layers and wicking layers for treating a particular tissue site.

In operation, according to some illustrative embodiments, the interface manifold 120 may be disposed against or proximate to the tissue site 104. The dressing 124 may be applied over or covering the interface manifold 120 and the tissue site 104 to form the sealed space 174. For example, the base layer 132 may be applied covering the interface manifold 120 and tissue surrounding the tissue site 104. The materials described above for the base layer 132 may have a tackiness that may hold the dressing 124 initially in position. The tackiness may be such that if an adjustment is desired, the dressing 124 may be removed and reapplied. Once the dressing 124 is in the desired position, a force may be applied, such as hand pressure, on a side of the sealing member 140 facing outward or opposite the tissue site 104. The force applied to the sealing member 140 may cause at least some portion of the adhesive 136 to penetrate or extend through the plurality of apertures 160 and into contact with tissue surrounding the tissue site 104, such as the epidermis 106, to releasably adhere the dressing 124 about the tissue site 104. In this manner, the configuration of the dressing 124 described above may provide an effective and reliable seal against challenging anatomical surfaces, such as an elbow or heal, at and around the tissue site 104. Further, the dressing 124 may permit re-application or re-positioning to, for example, correct air leaks caused by creases and other discontinuities in the dressing 124 and the tissue site 104. The ability to rectify leaks may increase the reliability of the therapy and reduce power consumption.

As the dressing 124 comes into contact with fluid from the tissue site 104, the fluid may move through the apertures 160 toward the fluid management assembly 144, 244. The fluid management assembly 144, 244 may wick or otherwise move the fluid away from the tissue site 104, and through the interface manifold 120, if equipped. As described above, the interface manifold 120 may be adapted to communicate fluid from the tissue site 104 rather than store the fluid. Thus, the fluid management assembly 144, 244 may be adapted to wick, pull, draw, or otherwise attract fluid from the tissue site 104 through the interface manifold 120. In the fluid management assembly 144, 244, the fluid may initially come into contact with the first dressing wicking layer 176, 276. The first dressing wicking layer 176, 276 may distribute the fluid laterally along the surface of the first dressing wicking layer 176, 276 for absorption or removal from the dressing 124. Similarly, fluid may come into contact with the second dressing wicking layer 180, 280 and may be distributed laterally along the surface of the second dressing wicking layer 180, 280 for absorption or removal from the dressing 124.

Figure 11:
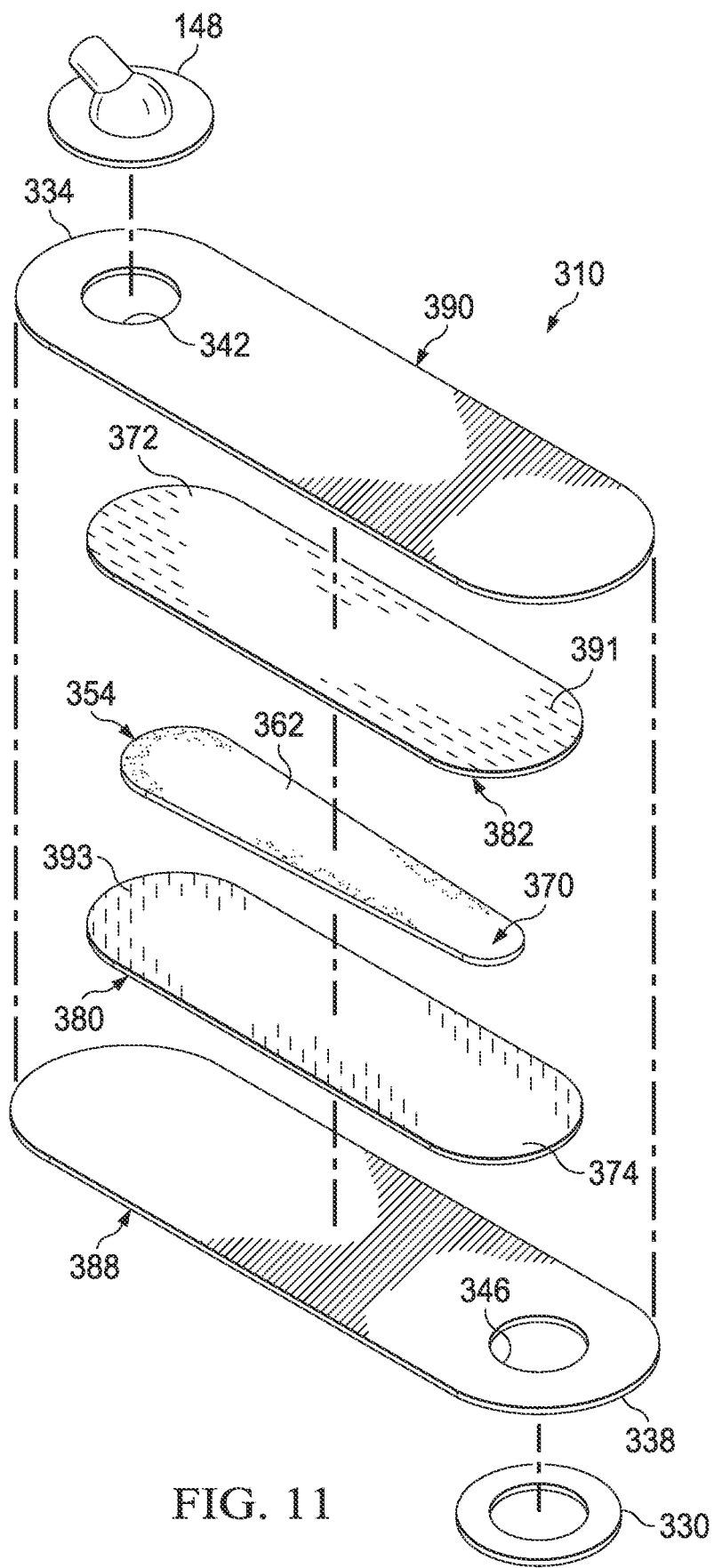
FIG. 11 is an exploded view of the bridge assembly of FIG. 9.

Referring to FIGS. 9-11, in some embodiments, a bridge assembly 310 may extend away from the tissue site 104 and the dressing 124 to define a fluid passageway between the tissue site 104 and the reduced-pressure source 128. For example, the bridge assembly 310 may be coupled in fluid communication between the dressing 124 and the reduced-pressure source 128. However, other applications for the bridge assembly 310 are possible. In some embodiments, the bridge assembly 310 may include a storage bridge 320, a sealing apparatus 330, and the conduit interface 148. It should be understood, that while dressing 124 is described with reference to FIGS. 9-11, dressings 324 or dressings 424, discussed herein, may additionally or alternatively be used with reference to FIGS. 9-11.

The storage bridge 320 may include a receiving end 334 separated or spaced apart from a transmitting end 338 by a length 340. The receiving end 334 may have a receiving end aperture 342, and the transmitting end 338 may have a transmitting end aperture 346. The receiving end 334 and the receiving end aperture 342 may be in fluid communication with the transmitting end 338 and the transmitting end aperture 346 through the length 340 of the storage bridge 320.

The conduit interface 148 may be adapted to be fluidly coupled to the receiving end 334 of the storage bridge 320 through, for example, the receiving end aperture 342. Thus, the conduit interface 148 may be in fluid communication with the transmitting end 338 through the length 340 of the storage bridge 320. The sealing apparatus 330 may be positioned about the transmitting end aperture 346 and between the transmitting end 338 and the dressing 124 for coupling the transmitting end 338 to the dressing 124 and in fluid communication with the dressing 124 through the transmitting end aperture 346. Thus, the conduit interface 148 may be positioned in fluid communication with the dressing 124 through the storage bridge 320. The sealing apparatus 330 may be any suitable device for making the connections described above, such as, without limitation, an adhesive ring or weld.

In some embodiments, the storage bridge 320 may include a bridge envelope 350, a bridge absorbent 354, and a bridge sealing member 358. The bridge envelope 350 may extend along the length 340 of the storage bridge 320. Further, the bridge envelope 350 may define an internal volume 360. The bridge absorbent 354 may be disposed within the internal volume 360 of the bridge envelope 350. In some embodiments, the bridge absorbent 354 may have a volume 362, in an unsaturated state, which is less than the internal volume 360 of the bridge envelope 350. In some embodiments, the bridge absorbent 354 may have a volume 362, in an unsaturated state, which is at least 5 percent less than the internal volume 360 of the bridge envelope 350. In some embodiments, the bridge absorbent 354 may have a volume 362, in an unsaturated state, which is at least 10 percent less than the internal volume 360 of the bridge envelope 350. In some embodiments, the bridge absorbent 354 may have a volume 362, in an unsaturated state, which is between 20 percent to about 90 percent of the internal volume 360 of the bridge envelope 350. In some embodiments, a cross-sectional area 364 of the bridge absorbent 354 may be less than a cross-sectional area 366 of the bridge envelope 350. The bridge absorbent 354 having a volume 362 or cross-sectional area 364 less than the internal volume 360 or cross-sectional area 366 of the bridge envelope 350 may allow for free movement of fluids and distribution of pressure around the bridge absorbent 354 when positioned within the internal volume 360 of the bridge envelope 350. In some embodiments, the bridge envelope 350 may entirely surround the bridge absorbent 354. Further, in some embodiments, the bridge envelope 350 may encapsulate the bridge absorbent 354. Further, in some embodiments, the bridge absorbent 354 may be moveable, expandable, or swellable within the internal volume 360 of the bridge envelope 350. For example, the bridge absorbent 354 may be configured to move, expand, or swell when the bridge absorbent 354 becomes fully or partially saturated with a liquid.

Further, the bridge envelope 350 may include an internal surface 368 and the bridge absorbent 354 may include an external surface 370. In some embodiments, at least a portion of the external surface 370 of the bridge absorbent 354 may be spaced apart or separated from the internal surface 368 of the bridge envelope 350. Further, in some embodiments, the entire external surface 370 of the bridge absorbent 354 may be separated or spaced apart from the internal surface 368 of the bridge envelope 350. Such a separation or space between the external surface 370 of the bridge absorbent 354 and the internal surface 368 of the bridge envelope 350 may occur, for example, as a result of fluids positioned between the external surface 370 and the internal surface 368 during operation.

In some embodiments, the bridge envelope 350 may include a fluid acquisition surface 372 and a fluid distribution surface 374. The fluid distribution surface 374 may be positioned opposite the fluid acquisition surface 372. The fluid distribution surface 374 may face the internal volume 360 of the bridge envelope 350 and the bridge absorbent 354. In some embodiments, at least a portion of the bridge absorbent 354 may be spaced apart from the fluid distribution surface 374 of the bridge envelope 350. In some embodiments, the fluid distribution surface 374 may include a plurality of longitudinal fibers 391 oriented substantially in a longitudinal direction along the length 340 of the storage bridge 320. Further, in some embodiments, the fluid acquisition surface 372 may include a plurality of vertical fibers 393 oriented substantially normal relative to the longitudinal fibers 391.

In some embodiments, the bridge envelope 350 may include a first bridge wicking layer 380 and a second bridge wicking layer 382. The first bridge wicking layer 380 and the second bridge wicking layer 382 may each extend along the length 340 of the storage bridge 320, and may be disposed within an internal passageway 384 that may be defined by the bridge sealing member 358. A periphery or edge of the first bridge wicking layer 380 may be coupled to a periphery or edge of the second bridge wicking layer 382 in any suitable manner, such as, for example, by a weld 386, to define the internal volume 360 of the bridge envelope 350. The bridge absorbent 354 may be positioned between the first bridge wicking layer 380 and the second bridge wicking layer 382. The first bridge wicking layer 380 and the second bridge wicking layer 382 may each include the fluid acquisition surface 372 and the fluid distribution surface 374. The fluid distribution surface 374 may be positioned on an opposite side of the first bridge wicking layer 380 and the second bridge wicking layer 382 from the fluid acquisition surface 372. Further, the fluid distribution surface 374 of the first bridge wicking layer 380 and the second bridge wicking layer 382 may face the bridge absorbent 354. In some embodiments, at least a portion of the bridge absorbent 354 may be spaced apart or separated from the fluid distribution surface 374 of the first bridge wicking layer 380 and the second bridge wicking layer 382.

In some embodiments, the bridge envelope 350 may comprise a non-woven material or structure such as, without limitation, a polyester, co-polyester, polyolefin, cellulosic fiber, and combinations or blends of the foregoing materials. In some embodiments, the bridge envelope 350 may comprise LIBELTEX TDL4 or LIBELTEX TDL2, or any of the materials recited above for the first dressing wicking layer 176 and the second dressing wicking layer 180. Further, in some embodiments, the bridge envelope 350 may comprise laminations with fiber or foam structures. The first bridge wicking layer 380 and the second bridge wicking layer 382 may each be comprised of the same materials recited above for the bridge envelope 350. In some embodiments, the bridge absorbent 354 may include a super-absorbent polymer or similar absorbent material, such as, without limitation, TEXSUS FP2325, or Gelok® 30040-76 S/S/S 300 gsm absorbent. Further, in some embodiments, the bridge absorbent 354 may comprise any of the materials recited above for the dressing absorbent 184.

The bridge sealing member 358 may encapsulate the bridge envelope 350, and may define the internal passageway 384. The internal passageway 384 may be in fluid communication between the receiving end 334 and the transmitting end 338 of the storage bridge 320. In some embodiments, the bridge sealing member 358 may entirely surround the bridge envelope 350. In some embodiments, the bridge envelope 350 may be disposed within the internal passageway 384 defined by the bridge sealing member 358. In some embodiments, the bridge sealing member 358 may sealingly enclose the bridge envelope 350 between the receiving end 334 and the transmitting end 338 of the storage bridge 320.

The bridge sealing member 358 may be comprised of similar materials described above for the dressing sealing member 140. For example, in some embodiments, the bridge sealing member 358 may comprise a substantially liquid impermeable film. Further, in some embodiments, the bridge sealing member 358 may comprise a vapor permeable film. Further, in some embodiments, the bridge sealing member 358 may comprise a breathable film. Additional examples of materials suitable for the bridge sealing member 358 may include, without limitation, a polyurethane drape or film such as Scapa Bioflex 130 polyurethane Film®; films formed from polymers, such as polyester and co-polyester; polyamide; polyamide/block polyether; acrylics; vinyl esters; polyvinyl alcohol copolymers; films with and without adhesive; and high Moisture Vapor Transfer Rate (MVTR) films, such as, for example, an INSPIRE 2305 polyurethane drape. High MVTR films may provide for evaporation of condensate, which may occur around the entire exterior surface of the storage bridge 320. In this manner, capacity, fluid handling, and evaporative properties of the storage bridge 320 may be enhanced or improved due at least to increased surface area and air movement provided around all sides and portions of the exterior surface of the storage bridge 320.

In some embodiments, the bridge sealing member 358 may include a first sealing layer 388 and a second sealing layer 390. A first periphery or edge of the first sealing layer 388 may be coupled to a second periphery or edge of the second sealing layer 390 around the bridge envelope 350 in any suitable manner, such as, for example, by a weld 392 for forming the bridge sealing member 358 and encapsulating the bridge envelope 350 therein. In other embodiments, the bridge sealing member 358 may be formed from a single layer of material.

The bridge assembly 310 may include features to indicate a level of fluid retained in the storage bridge 320. For example, the storage bridge 320 may include a fluid capacity indicator 394 or a plurality of fluid capacity indicators 394 positioned along the length 340 of the storage bridge 320. In some embodiments, the fluid capacity indicators 394 may be positioned sequentially along the length 340 of the storage bridge 320 to indicate an amount of fluid present or fluid capacity remaining in the storage bridge 320. The fluid capacity indicators 394 may each identify a fraction or percentage of the total fluid capacity of the storage bridge 320. Further, in some embodiments, a liquid changing dye (not shown) may be positioned within the internal passageway 384 defined by the bridge sealing member 358 in any suitable manner, such as, for example, as a coating, layer, or particulate. The liquid changing dye may also indicate a level of fluid retained in the storage bridge 320. Materials suitable for use as the liquid changing dye may include, without limitation, water soluble or swellable polymers, such as polyvinyl alcohol and copolymers; acrylics; polyurethanes; and soluble salts, such as sodium, potassium, and sodium acrylate. Water soluble dyes, such as, for example, indigo carmine or fast green FCF, may be mixed into the water soluble polymers set forth above. Such a compound may swell or dissolve when exposed to fluid, which may release the dye, indicating the fluid level in the storage bridge 320.

In operation, the reduced-pressure source 128 may be fluidly coupled to the receiving end 334 of the storage bridge 320. For example, the conduit interface 148 may be fluidly coupled to the receiving end 334, and the conduit 196 may be fluidly coupled between the conduit interface 148 and the reduced-pressure source 128 analogous to the previously described embodiments. The transmitting end 338 of the storage bridge 320 may be fluidly coupled to the dressing 124 as described above. The reduced-pressure source 128 may be activated to provide reduced pressure to the dressing 124 through the storage bridge 320, which may draw, wick, or pull fluids from the tissue site 104 and the dressing 124 into the storage bridge 320.

The structure of the storage bridge 320 may be configured to be more hydrophilic or absorbent than the dressing 124. For example, in some previously described embodiments, the dressing 124 may be configured without an absorbent while the storage bridge 320 is configured with the bridge absorbent 354. In other embodiments, the dressing 124 may include components that possess some absorbency, but less absorbency than the storage bridge 320. Accordingly, the system 102 may be configured with an absorbent gradient that increases in absorbency or hydrophilicity with increasing distance away from the tissue site 104, such as, for example, from the dressing 124 toward the reduced-pressure source 128. Therefore, fluids may be drawn from the tissue site 104 into the storage bridge 320 by the application of the reduced pressure and by operation of attractive forces that may be exerted on the fluid by the absorbent gradient.

As fluid enters the storage bridge 320, the fluid may first contact portions of the bridge absorbent 354 near the transmitting end 338 of the storage bridge 320, which may become saturated with the fluid or blocked. Such fluid saturation or blockage near the transmitting end 338 of the storage bridge 320 may force the fluid to move along the length 340 of the storage bridge 320, between the external surface 370 of the storage bridge 320 and the internal surface 368 of the bridge envelope 350, toward the receiving end 334 of the storage bridge 320 for absorption. The internal surface 368 of the bridge envelope 350 may also be the fluid distribution surface 374 of the bridge envelope 350, which may enhance the movement and distribution of the fluid within the internal volume 360 of the bridge envelope 350 and the bridge absorbent 354. The fluid may also wick or travel along the fluid acquisition surface 372 along the length 340 of the storage bridge 320 and pass through or permeate the bridge envelope 350 to the fluid distribution surface 374 for distribution to the bridge absorbent 354. The fluid may continue to travel in this manner along the length 340 of the storage bridge 320 from the transmitting end 338 to the receiving end 334 until the storage bridge 320 reaches full fluid capacity. Portions of the storage bridge 320 that become saturated or blocked with fluid may swell and serve as an indication of the level of fluid contained in the storage bridge 320. The fluid capacity indicator 394 and the liquid changing dye may also provide an indication of fluid capacity as described above.

Figure 12:
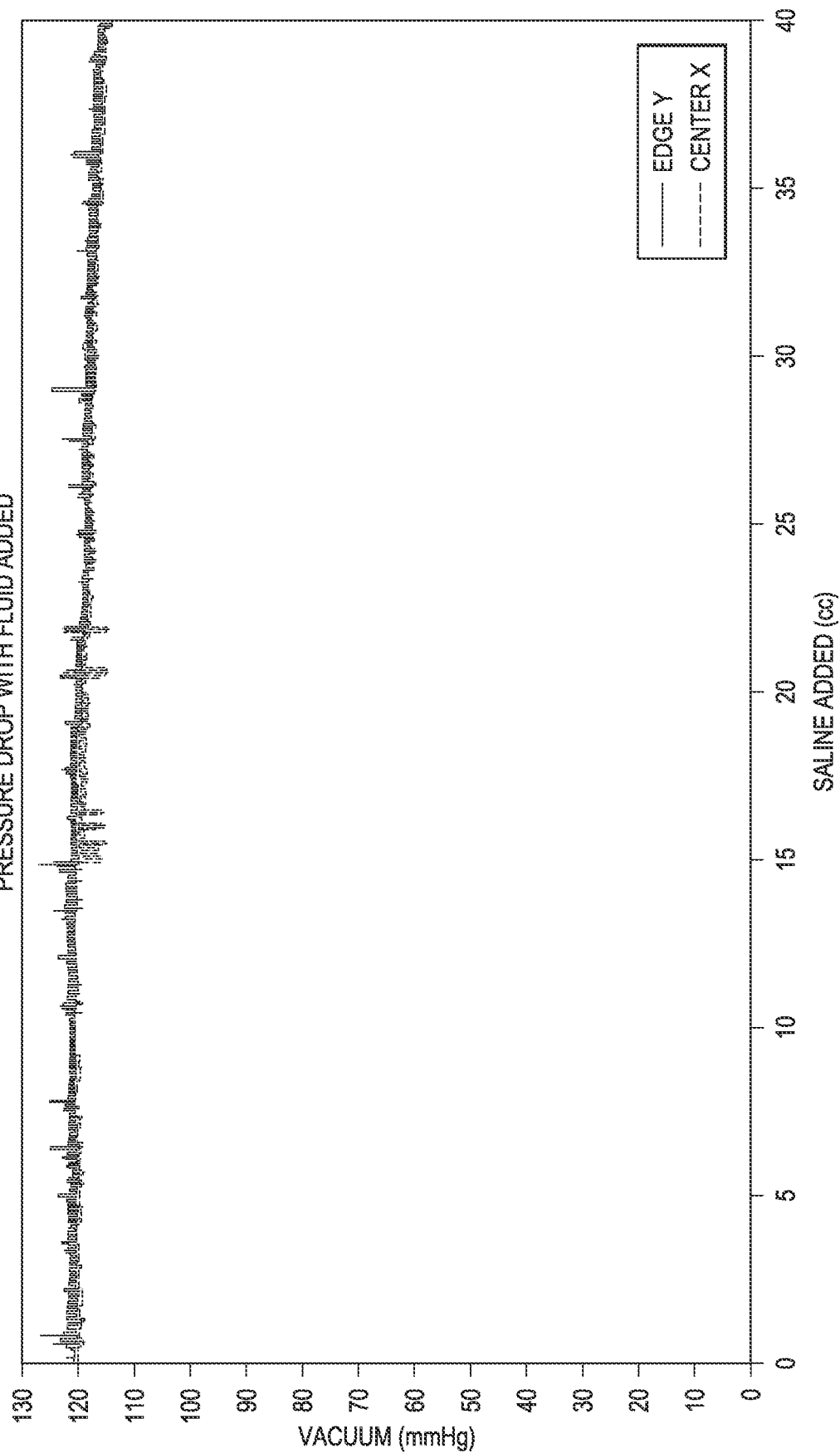
FIG. 12 is a graph illustrating reduced pressure communication to a dressing through a bridge assembly according to this disclosure during application of fluid to the dressing.

Referring to FIG. 12, a graphical plot of pressure in the dressing 124 versus fluid volume is shown as a result of performance testing. In the testing, the storage bridge 320 was assembled with the dressing 124 according to this disclosure. The storage bridge 320 was held in a vertical position, and a reduced pressure of 125 mmHg was applied to the dressing 124 through the storage bridge 320. Pressure measurements were taken in the dressing 124 at an edge Y and a center X of the dressing 124, shown in FIG. 9, during delivery of saline fluid to the dressing 124 at a rate of 0.83 cc per hour. As shown in FIG. 12, the measured pressure remained stable between about 115 mmHg to about 125 mmHg, illustrating that no significant drop in reduced pressure occurred in the system 102 or though the storage bridge 320 during the addition of the saline in the testing.

Among other benefits described above, the storage bridge 320 may reduce power consumption, leakage, and other challenges that may be associated with fluid head pressure caused by a static column of fluid that can reside in a conventional tube or similar structure providing fluid communication between a dressing and a reduced-pressure source. Further, a mass of fluid removed from a tissue site may be moved away from the surface of the tissue site. The storage bridge 320 may also provide a low-profile and conformable solution for providing fluid communication with a tissue site, which may enhance patient comfort.

Figure 13:
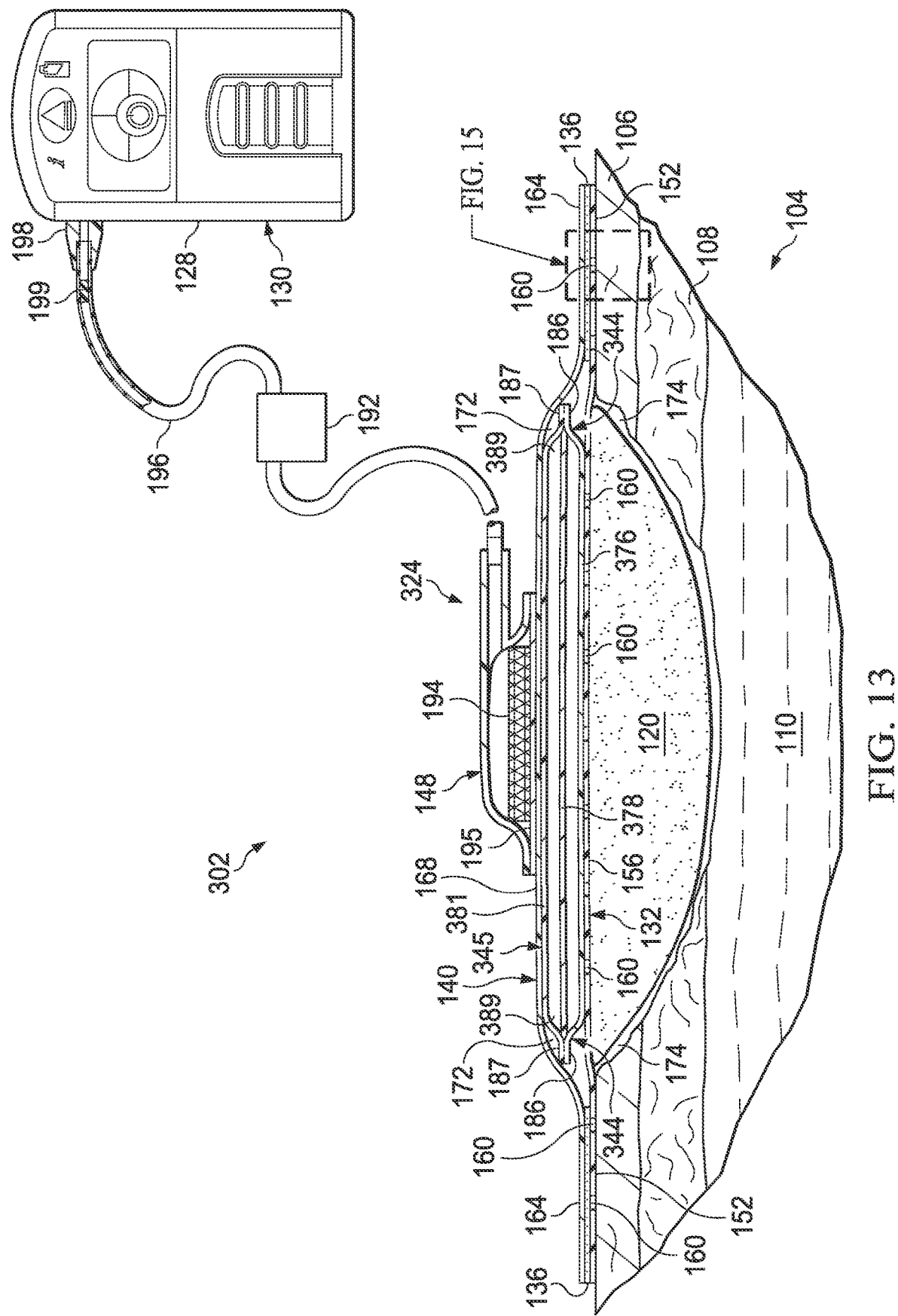
FIG. 13 is a cut-away view of an illustrative example of a system for treating a tissue site depicting another illustrative example of a dressing deployed at the tissue site.
Figure 16A:
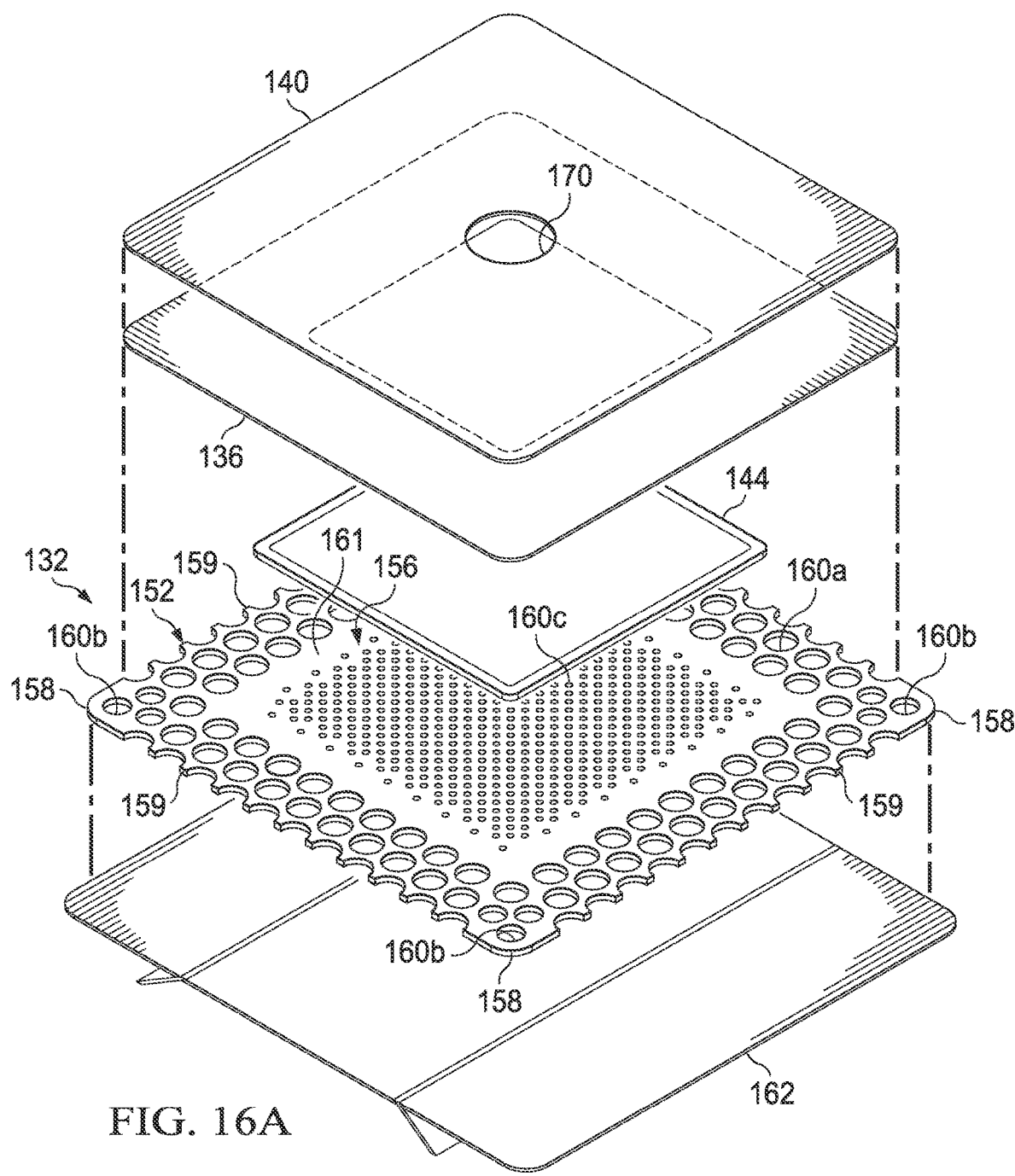
FIG. 16A is an exploded view of the dressing of FIG. 13, depicted without a conduit interface and with an illustrative example of a release liner for protecting the dressing prior to application at the tissue site.
Figure 16B:
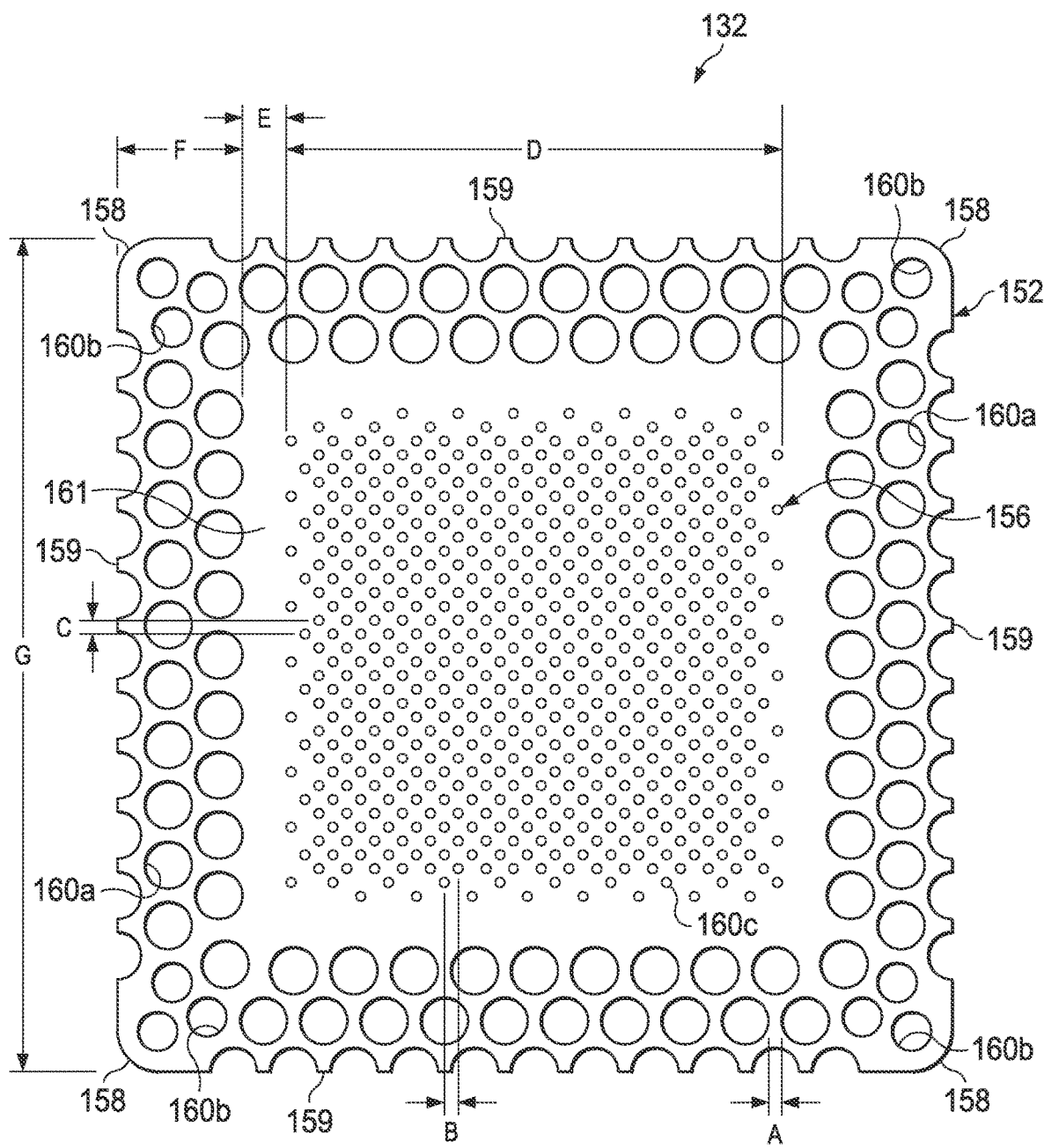
FIG. 16B is a plan view of an illustrative example of a base layer depicted in the dressing of FIG. 16A.

Referring to the drawings, FIG. 13 depicts an illustrative embodiment of a system 302 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 13 that may extend below the surface of the epidermis 106. Further, the tissue site 104 may be a surface tissue site (not shown) that may predominantly reside on the surface of the epidermis 106, such as, for example, an incision. The system 302 may provide therapy to, for example, the epidermis 106, the dermis 108, and the subcutaneous tissue 110, regardless of the positioning of the system 302 or the type of tissue site. The system 302 may be used to treat wound and shallow wounds on a patient such as venous leg ulcers (VLUs). The system may also be attached to a patient over or near a wound and compressed against tissue at or near the wound using bandages and/or compression garments (such as a compression garment with a hydrophobic coating). A compression garment (such as a compression garment with a hydrophobic coating) may prevent evaporated fluid from pooling in the dressing of the system 302, reduce the likelihood of infection, and the negative impact on patient wellbeing as a result of odor. In some embodiments, a compression garment may include an activated charcoal component to mitigate odor. The activated charcoal component may increase evaporation rates from the dressing of the system 302 as fluid molecules will be drawn to the coated compression garment. The system 302 under compression against tissue may provide a low profile on a patient. The system 302 may also be used without limitation at other tissue sites.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 104 may include the removal of fluids, such as exudate or ascites.

Continuing with FIG. 13, the system 302 may include an optional tissue interface, such as an interface manifold 120. Further, the system 302 may include a dressing 324 and a reduced-pressure source 128. The reduced-pressure source 128 may be a component of an optional therapy unit 130. In some embodiments, the reduced-pressure source 128 and the therapy unit 130 may be separate components. Further, in some embodiments, the interface manifold 120 may be omitted for different types of tissue sites or different types of therapy, such as, for example, epithelialization. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104. In some embodiments, the interface manifold 120 may be positioned in direct contact with the tissue site 104.

The tissue interface or the interface manifold 120 may be formed from any manifold material or flexible bolster material that provides a vacuum space, or treatment space, such as, for example, a porous and permeable foam or foam-like material, a member formed with pathways, a graft, a non-adherent material, a non-adherent copolymer mesh, or a gauze. In some embodiments, the interface manifold 120 may be a reticulated, open-cell polyurethane or polyether foam that may be fluid permeable while under a reduced pressure. One such foam material is VAC® GranuFoam® material available from Kinetic Concepts, Inc. (KCI) of San Antonio, Texas. Further, in some embodiments, any material or combination of materials may be used as a manifold material for the interface manifold 120 provided that the manifold material is operable to distribute or collect fluid. For example, herein the term manifold may refer to a substance or structure configured for delivering fluids to or removing fluids from a tissue site through a plurality of pores, pathways, or flow channels. The plurality of pores, pathways, or flow channels may be interconnected to improve the distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, a material with a higher or lower density than GranuFoam® material may be desirable for the interface manifold 120 depending on the application. Among the many possible materials, the following may be used without limitation: GranuFoam® material; Foamex® technical foam (www.foamex.com); a molded bed of nails structure; a patterned grid material, such as those manufactured by Sercol Industrial Fabrics; 3D textiles, such as those manufactured by Baltex of Derby, U.K.; a gauze; a flexible channel-containing member; or a graft. Further, in some embodiments, ionic silver may be added to the interface manifold 120 by, for example, a micro bonding process. Other substances, such as anti-microbial agents, may be added to the interface manifold 120 as well.

In some embodiments, the interface manifold 120 may comprise a porous, hydrophobic material. The hydrophobic characteristics of the interface manifold 120 may prevent the interface manifold 120 from directly absorbing fluid, such as exudate, from the tissue site 104, but allow the fluid to pass through.

In some embodiments, the dressing 324 may include a base layer 132, an adhesive 136, a sealing member 140, a fluid management assembly 344, and a conduit interface 148. Components of the dressing 324 may be added or removed to suit a particular application. In some embodiments, the dressing 324 may be adapted to provide reduced pressure from the reduced-pressure source 128 to the interface manifold 120, and to extract fluid from the tissue site 104 through the interface manifold 120.

Referring to FIGS. 13-16B, the base layer 132 may have a periphery 152 surrounding a central portion 156, and a plurality of apertures 160 disposed through the periphery 152 and the central portion 156. The base layer 132 may also have corners 158 and edges 159. The corners 158 and the edges 159 may be part of the periphery 152. One of the edges 159 may meet another of the edges 159 to define one of the corners 158. Further, the base layer 132 may have a border 161 substantially surrounding the central portion 156 and positioned between the central portion 156 and the periphery 152. In some embodiments, the border 161 may be free of the apertures 160. In some embodiments, the base layer 132 may be adapted to cover the interface manifold 120 and tissue surrounding the tissue site 104 such that the central portion 156 of the base layer 132 is positioned adjacent to or proximate to the interface manifold 120, and the periphery 152 of the base layer 132 is positioned adjacent to or proximate to tissue surrounding the tissue site 104. In such embodiments, the periphery 152 of the base layer 132 may surround the interface manifold 120. Further, the apertures 160 in the base layer 132 may be in fluid communication with the interface manifold 120 and tissue surrounding the tissue site 104.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. Each of the apertures 160 of the plurality of apertures 160 may be substantially circular in shape, having a diameter and an area. The area of the apertures 160 described in the illustrative embodiments herein may be substantially similar to the area in other embodiments for the apertures 160 that may have non-circular shapes. Further, the area of each of the apertures 160 may be substantially the same, or each of the areas may vary, for example, based on the position of the aperture 160 in the base layer 132. For example, the area of the apertures 160 in the periphery 152 of the base layer 132 may be larger than the area of the apertures 160 in the central portion 156 of the base layer 132. The apertures 160 may have a uniform pattern or may be randomly distributed on the base layer 132. The size and configuration of the apertures 160 may be designed to control the adherence of the dressing 124 to the epidermis 106 as described herein.

In some embodiments, the apertures 160 positioned in the periphery 152 may be apertures 160a, the apertures 160 positioned at the corners 158 of the periphery 152 may be apertures 160b, and the apertures 160 positioned in the central portion 156 may be apertures 160c. In some embodiments, the apertures 160a may have an area greater than the apertures 160b. Further, in some embodiments, the apertures 160b may have an area greater than the apertures 160c. The dimensions of the base layer 132 may be increased or decreased, for example, substantially in proportion to one another to suit a particular application. Further, although the central portion 156, the border 161, and the periphery 152 of the base layer 132 are shown as having a substantially square shape, these and other components of the base layer 132 may have any shape to suit a particular application.

The base layer 132 may be a soft, pliable material suitable for providing a fluid seal with the tissue site 104 as described herein. For example, the base layer 132 may comprise a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive as described below, polyurethane, polyolefin, or hydrogenated styrenic copolymers. In some embodiments, the base layer 132 may include a silicone such as Scapa Soft-Pro®. The base layer 132 may have a thickness between about 500 microns (μm) and about 1000 microns (μm). In some embodiments, the base layer 132 may have a stiffness between about 5 Shore OO and about 80 Shore OO. Further, in some embodiments, the base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. The base layer 132 may additionally or alternatively be a non-adherent copolymer mesh. In this manner, the adhesive 136 may extend through openings in the spaced material analogous to the apertures 160.

In some embodiments, the adhesive 136 may be exposed to the apertures 160 in at least the periphery 152 of the base layer 132. Further, in some embodiments, the adhesive 136 may be positioned adjacent to, or positioned in fluid communication with, the apertures 160 in at least the periphery 152 of the base layer 132. Further, in some embodiments, the adhesive 136 may be exposed to or in fluid communication with tissue surrounding the tissue site 104 through the apertures 160 in the base layer 132. As described herein and shown in FIG. 15, the adhesive 136 may extend, deform, or be pressed through the plurality of apertures 160 to contact the epidermis 106 for securing the dressing 324 to, for example, tissue surrounding the tissue site 104. The apertures 160 may provide sufficient contact of the adhesive 136 to the epidermis 106 to secure the dressing 124 about the tissue site 104. However, the configuration of the apertures 160 and the adhesive 136, described herein, may permit release and repositioning of the dressing 324 about the tissue site 104.

In some embodiments, the apertures 160b at the corners 158 of the periphery 152 may be smaller than the apertures 160a in other portions of the periphery 152. For a given geometry of the corners 158, the smaller size of the apertures 160b compared to the apertures 160a may enhance or increase the surface area of the adhesive 136 exposed to the apertures 160b and to tissue through the apertures 160b at the corners 158. The size and number of the apertures 160b in the corners 158 may be adjusted as necessary, depending on the chosen geometry of the corners 158, to enhance or increase the exposed surface area of the adhesive 136 as described above.

Similar to the apertures 160b in the corners 158, any of the apertures 160 may be adjusted in size and number to increase the surface area of the adhesive 136 exposed to or in fluid communication with the apertures 160 for a particular application or geometry of the base layer 132. For example, in some embodiments (not shown) the apertures 160b, or apertures of another size, may be positioned in the periphery 152 and at the border 161. Similarly, the apertures 160b, or apertures of another size, may be positioned as described above in other locations of the base layer 132 that may have a complex geometry or shape.

The adhesive 136 may be a medically-acceptable adhesive. In some embodiments, the adhesive 136 may be deformable or flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive. The adhesive 136 may be a layer having substantially the same shape as the periphery 152 of the base layer 132. In some embodiments, the adhesive 136 may be continuous or discontinuous. Discontinuities in the adhesive 136 may be provided by apertures (not shown) in the adhesive 136. Apertures in the adhesive 136 may be formed after application of the adhesive 136 or by coating the adhesive 136 in patterns on a carrier layer, such as, for example, a side of the sealing member 140 adapted to face the epidermis 106. Further, apertures in the adhesive 136 may be sized to control the amount of the adhesive 136 extending through the apertures 160 in the base layer 132 to reach the epidermis 106. Apertures in the adhesive 136 may also be sized to enhance the Moisture Vapor Transfer Rate (MVTR) of the dressing 124, described further herein.

Factors that may be utilized to control the adhesion strength of the dressing 324 may include the diameter, area, and number of the apertures 160 in the base layer 132, the thickness of the base layer 132, the thickness and amount of the adhesive 136, and the tackiness of the adhesive 136. An increase in the amount of the adhesive 136 extending through the apertures 160 may correspond to an increase in the adhesion strength of the dressing 324. A decrease in the thickness of the base layer 132 may correspond to an increase in the amount of adhesive 136 extending through the apertures 160. Thus, the diameter, area, and configuration of the apertures 160, the thickness of the base layer 132, and the amount and tackiness of the adhesive utilized may be varied to provide a desired adhesion strength for the dressing 324.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b and 160c. In this manner, locations of the base layer 132 having larger apertures 160 and lower tackiness adhesive 136 may have an adhesion strength comparable to locations having smaller apertures 160 and higher tackiness adhesive 136.

A release liner 162 may be attached to or positioned adjacent to the base layer 132 to protect the adhesive 136 prior to application of the dressing 324 to the tissue site 104. Prior to application of the dressing 324 to the tissue site 104, the base layer 132 may be positioned between the sealing member 140 and the release liner 162. Removal of the release liner 162 may expose the base layer 132 and the adhesive 136 for application of the dressing 324 to the tissue site 104. The release liner 162 may also provide stiffness to assist with, for example, deployment of the dressing 324. The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 324. For example, the polar semi-crystalline polymer may be highly orientated and resistant to softening, swelling, or other deformation that may occur when brought into contact with components of the dressing 324, or when subjected to temperature or environmental variations, or sterilization. Further, a release agent may be disposed on a side of the release liner 162 that is configured to contact the base layer 132. For example, the release agent may be a silicone coating and may have a release factor suitable to facilitate removal of the release liner 162 by hand and without damaging or deforming the dressing 324. In some embodiments, the release agent may be fluorosilicone. In other embodiments, the release liner 162 may be uncoated or otherwise used without a release agent. In some embodiments, the base layer 132 may be adapted to be positioned in direct contact with the tissue site 104. In some embodiments, the base layer 132 may include a non-adherent mesh and one or more wicking layers of the dressing as discussed herein may be positioned between the base layer 132 and a dressing sealing member as discussed herein.

Continuing with FIGS. 13-16B, the sealing member 140 may also be referred to as a dressing sealing member 140. The sealing member 140 may have a periphery 164 and a central portion 168. The sealing member 140 may additionally include an aperture 170. The periphery 164 of the sealing member 140 may be positioned proximate to the periphery 152 of the base layer 132 such that the central portion 168 of the sealing member 140 and the central portion 156 of the base layer 132 define an enclosure 172. The adhesive 136 may be positioned at least between the periphery 164 of the sealing member 140 and the periphery 152 of the base layer 132. The sealing member 140 may cover the tissue site 104 and the interface manifold 120 to provide a fluid seal and a sealed space 174 between the tissue site 104 and the sealing member 140 of the dressing 324. Further, the sealing member 140 may cover other tissue, such as a portion of the epidermis 106, surrounding the tissue site 104 to provide the fluid seal between the sealing member 140 and the tissue site 104. In some embodiments, a portion of the periphery 164 of the sealing member 140 may extend beyond the periphery 152 of the base layer 132 and into direct contact with tissue surrounding the tissue site 104. In other embodiments, the periphery 164 of the sealing member 140, for example, may be positioned in contact with tissue surrounding the tissue site 104 to provide the sealed space 174 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal may be a seal adequate to maintain reduced pressure at a desired site given the particular reduced pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, California; a polyurethane (PU) film such as Scapa Bioflex 130 polyurethane Film®; polyether block polyamide copolymer (PEBAX), for example, from Arkema, France; Expopack 2327; or other appropriate material.

The sealing member 140 may be vapor permeable and liquid impermeable, thereby allowing vapor and inhibiting liquids from exiting the sealed space 174 provided by the dressing 324. In some embodiments, the sealing member 140 may be a flexible, breathable film, membrane, or sheet having a high MVTR of, for example, at least about 300 g/m$^2$ per 24 hours. In other embodiments, a low or no vapor transfer drape may be used. The sealing member 140 may comprise a range of medically suitable films having a thickness between about 15 microns (μm) to about 50 microns (μm).

The fluid management assembly 344 may be disposed in the enclosure 172. In some embodiments, the fluid management assembly 344 may include one or more dressing wicking layers 345. For example, a first dressing wicking layer 376, a second dressing wicking layer 378, and a third dressing wicking layer 381. The one or more dressing wicking layers 345 may wick fluid along a surface of one or more of the first dressing wicking layer 376, the second dressing wicking layer 378, and the third dressing wicking layer 381. For example, one or more dressing wicking layer 345 may wick or otherwise transport fluid in a lateral direction along the surfaces of one of the first dressing wicking layer 376, the second dressing wicking layer 378, or the third dressing wicking layer 381, respectively. The surface of the first dressing wicking layer 376 may be normal relative to the thickness of the first dressing wicking layer 176. The surface of the second dressing wicking layer 378 may be normal relative to the thickness of the second dressing wicking layer 378. The surface of the third dressing wicking layer 381 may be normal relative to the thickness of the third dressing wicking layer 381. The wicking of fluid along the one or more dressing wicking layers 345 may enhance the distribution of the fluid. A laminate combination of the first dressing wicking layer 376, the second dressing wicking layer 378, and the third dressing wicking layer 381 may be adapted as described herein to maintain an open structure, resistant to blockage, capable of maintaining fluid communication with, for example, the tissue site 104.

Figure 17:
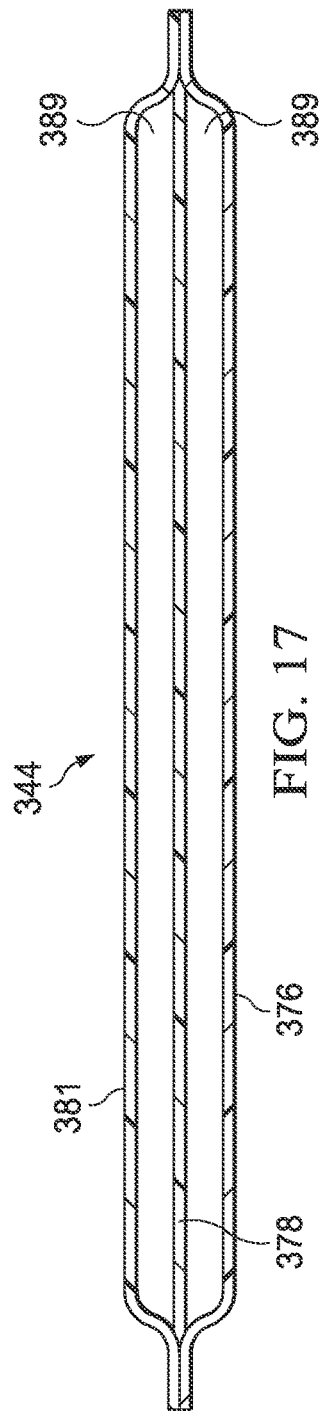
FIG. 17 is a cut-away view of an illustrative example of a fluid management assembly suitable for use with the dressing and system of FIG. 13.

Referring to the embodiments of the fluid management assembly 344 depicted in FIGS. 13, 14, and 17, a peripheral portion 186 of the first dressing wicking layer 376 may be coupled to a peripheral portion 187 of the third dressing wicking layer 381 to define a wicking layer enclosure 389 between the first dressing wicking layer 376 and the third dressing wicking layer 381. In some embodiments, the wicking layer enclosure 389 may surround or otherwise encapsulate the second dressing wicking layer 378 between the first dressing wicking layer 376 and the third dressing wicking layer 381. Materials suitable for the first dressing wicking layer 376, the second dressing wicking layer 378, and the third dressing wicking layer 381 may include, without limitation, any material having a grain structure capable of wicking fluid as described herein, such as, for example, LIBELTEX TDL2, 80 gsm, or similar materials, which may be non-woven.

The fluid management assembly 344 may be manufactured as a pre-laminated structure, or supplied as individual layers of material that can be stacked upon one another as described above. Individual layers of the fluid management assembly 344 may be bonded or otherwise secured to one another without adversely affecting fluid management by, for example, utilizing a solvent or non-solvent adhesive, or by thermal welding. Further, the fluid management assembly 344 may be coupled to the border 161 of the base layer 132 in any suitable manner, such as, for example, by a weld or an adhesive. The border 161, being free of the apertures 160 as described above, may provide a flexible barrier between the fluid management assembly 344 and the tissue site 104 for enhancing comfort. In some embodiments, the base layer 132 may include a non-adherent interface. The non-adherent interface may be used with VLUs to accommodate a sensitive and/or a sore tissue site. The non-adherent interface may include a co-polymer mesh.

The dressing 324 may be modified in various embodiments to suit a particular application. The first dressing wicking layer 376, the second dressing wicking layer 378, and the third dressing wicking layer 381 may wick or draw fluid away from the tissue site 104 for transport to a location exterior to the dressing 324. Further, the configuration of the first dressing wicking layer 376, the second dressing wicking layer 378, and the third dressing wicking layer 381 described herein may preference fluid away from the tissue site 104 and prevent the fluid from returning to the tissue site 104 prior to removal of the fluid from the dressing 324, for example, by the application of reduced pressure. The wicking layer enclosure 389 may enhance this ability to preference fluid away from the tissue site 104 and to prevent the fluid from returning to the tissue site 104. In some embodiments, the dressing 324 may comprise a winged profile to allow for greater adhesion between the dressing 324 and a leg or an arm, for example.

The dressing 324 may be further modified in various embodiments that may be suitable for some applications that communicate fluid from the tissue site 104 exterior to the dressing 324. For example, the fluid management assembly 344 may be omitted from the dressing 324, and a dressing manifold (not shown) may be positioned in the enclosure 172 in place of the fluid management assembly 344. The dressing manifold may be configured as a layer and may be comprised of any material suitable for removing fluids from a tissue site through a plurality of pores, pathways, or flow channels as described herein, such as, without limitation, a foam, a woven material, a cast silicone, a polyurethane material, or any of the materials recited above for the interface manifold 120. Further, in some embodiments, the dressing 324 may be modified by omitting the base layer 132 and replacing the fluid management assembly 344 with the above-described dressing manifold. In such an embodiment, the dressing 324 may comprise the sealing member 140 and the dressing manifold for disposing in the sealed space 174 between the sealing member 140 and the tissue site 104.

In some embodiments, the fluid management assembly 344 may include a film, a first wicking layer, and a second wicking layer. The film may be a base layer of adhesive coated polyurethane (PU) film. The adhesive coated on the film may adhere the first wicking layer to an inner surface of the fluid management assembly (i.e. a surface forming the wicking layer enclosure 188 and exposed to the wicking layer enclosure 188). The first wicking layer may be stacked or placed below or underneath the second wicking layer such that fluid (such a fluid of exudate) is communicated from the first wicking layer to the second wicking layer and out the conduit interface 148. The first wicking layer may have a wider base and a higher density relative to the second wicking layer. The first wicking layer may have a surface area that is greater than a surface area of the second wicking layer. The first wicking layer may have a greater thickness (such as 50 mm) relative to the second wicking layer thickness (such as 20 mm). The first wicking layer may include a profile to spread the fluid out over an entire surface of the first wicking layer to increase evaporation. The second wicking layer may be used to pull fluid from the wound towards to the conduit interface 148. In some embodiments, the second wicking layer may alternatively or additionally include a profile like the profile of the first wicking layer to spread fluid out over an entire surface of the second wicking layer. The profile of the second wicking layer may also be used to increase evaporation. In some embodiments, the fluid management assembly 344 may include a film positioned to adhere to the second wicking layer on a surface of the second wicking layer opposite the first wicking layer. The film positioned to adhere to the second wicking layer may include one or more of the same properties as the film that may adhere to the first wicking layer described herein.

Figure 18:
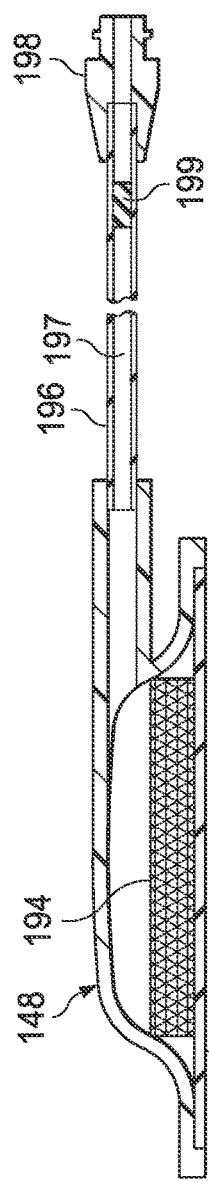
FIG. 18 is a cut-away view of an illustrative example of a conduit interface shown with the dressing of FIG. 13.

Referring to FIGS. 13, 14, and 18, the conduit interface 148 may be positioned proximate to the sealing member 140 and in fluid communication with the enclosure 172 of the dressing 324. For example, the conduit interface 148 may be in fluid communication with the dressing 324 through the aperture 170 in the sealing member 140. The conduit interface 148 may provide reduced pressure from the reduced-pressure source 128 to the dressing 324. The conduit interface 148 may also be adapted to be positioned in fluid communication with the optional interface manifold 120. An optional liquid trap 192 may be positioned in fluid communication between the dressing 324 and the reduced-pressure source 128. The liquid trap 192 may be any suitable containment device having a sealed internal volume capable of retaining liquid, such as condensate or other liquids.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene. In some illustrative, non-limiting embodiments, conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the dressing 324 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 302. Further, the absorbent material or hydrophilic polymer may be suitable for use in various components of the system 302 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 302, relative to the temperature at the tissue site 104. Removal or dissipation of liquids from the conduit interface 148 may increase visual appeal and prevent odor. Further, such removal of liquids may also increase efficiency and reliability by reducing blockages and other interference with the components of the system 302.

Similar to the conduit interface 148, the liquid trap 192, and other components of the system 302, may also be formed of an absorbent material or a hydrophilic polymer. The absorptive and evaporative properties of the hydrophilic polymer may also facilitate removal and dissipation of liquids residing in the liquid trap 192, and other components of the system 302, by evaporation. Such evaporation may leave behind a substantially solid or gel-like waste. The substantially solid or gel-like waste may be cheaper to dispose than liquids, providing a cost savings for operation of the system 302. The hydrophilic polymer may be used for other components in the system 302 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 302 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 302. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

The conduit interface 148 may carry an odor filter 194 adapted to substantially preclude the passage of odors from the tissue site 104 out of the sealed space 174. Further, the conduit interface 148 may carry a primary hydrophobic filter 195 adapted to substantially preclude the passage of liquids through the primary hydrophobic filter 195. The odor filter 194 and the primary hydrophobic filter 195 may be disposed in the conduit interface 148 or other suitable location such that fluid communication between the reduced-pressure source 128, or optional therapy unit 130, and the dressing 324 is provided through the odor filter 194 and the primary hydrophobic filter 195. In some embodiments, the odor filter 194 and the primary hydrophobic filter 195 may be secured within the conduit interface 148 in any suitable manner, such as by adhesive or welding. In other embodiments, the odor filter 194 or the primary hydrophobic filter 195 may be omitted, or positioned proximate to any exit location in the system 302 or the dressing 324 that is in fluid communication with the atmosphere, the reduced-pressure source 128, or the optional therapy unit 130.

The odor filter 194 may be comprised of a carbon material in the form of a layer or particulate. For example, the odor filter 194 may comprise a woven carbon cloth filter such as those manufactured by Chemviron Carbon, Ltd. of Lancashire, United Kingdom. The primary hydrophobic filter 195 may be comprised of a material that is liquid impermeable and vapor permeable. For example, the primary hydrophobic filter 195 may comprise a material manufactured under the designation MMT-314 by W.L. Gore & Associates, Inc. of Newark, Delaware, United States, or similar materials. The primary hydrophobic filter 195 may be provided in the form of a membrane or layer.

Continuing with FIGS. 13, 14, and 18, the reduced-pressure source 128 may provide reduced pressure to the dressing 324 and the sealed space 174. The reduced-pressure source 128 may be any suitable device for providing reduced pressure, such as, for example, a vacuum pump, wall suction, hand pump, manual pump, or other source. In some embodiments, the reduced-pressure source 128 may be a component of the therapy unit 130. The therapy unit 130 may include control circuitry and sensors, such as a pressure sensor, that may be configured to monitor reduced pressure at the tissue site 104. The therapy unit 130 may also be configured to control the amount of reduced pressure from the reduced-pressure source 128 being applied to the tissue site 104 according to a user input and a reduced-pressure feedback signal received from the tissue site 104. In some embodiments, the reduced pressure source 128 (such as a manual pump, hand pump, or the like) may comprise a container or may be fluidly connected to a container that receives fluid collected from the tissue site 104. Thus, when the reduced pressure source 128 generates reduced pressure, fluid may be communicated from the tissue site, through the dressing, through the bridge, and received and stored in the container of the reduced pressure source 128 or fluidly connected to the reduced pressure source 128.

As used herein, "reduced pressure" may refer to a pressure less than the ambient pressure at a tissue site being subjected to treatment. In some embodiments, the reduced pressure may be less than the atmospheric pressure. Further, in some embodiments, the reduced pressure may also be less than a hydrostatic pressure at a tissue site. Unless otherwise indicated, values of pressure stated herein are gauge pressures. While the amount and nature of reduced pressure applied to a tissue site may vary according to the application, in some embodiments, the reduced pressure may be between −5 mm Hg and −500 mm Hg. In some embodiments, the reduced pressure may be between −100 mm Hg and −200 mm Hg.

The reduced pressure delivered may be, for example, constant, varied, patterned, or random. Further, the reduced pressure may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refer to a relative reduction in absolute pressure. Further, an increase in reduced pressure may correspond to a reduction in pressure (more negative relative to ambient pressure), and a decrease in reduced pressure may correspond to an increase in pressure (less negative relative to ambient pressure).

Referring to FIGS. 13 and 18, a conduit 196 having an internal lumen 197 may be coupled in fluid communication between the reduced-pressure source 128 and the dressing 324. The internal lumen 197 may have an internal diameter between about 0.5 millimeters to about 3.0 millimeters. In some embodiments, the internal diameter of the internal lumen 197 may be between about 1 millimeter to about 2 millimeters. The conduit interface 148 may be coupled in fluid communication with the dressing 324 and adapted to connect between the conduit 196 and the dressing 324 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The aperture 170 in the sealing member 140 may provide fluid communication between the dressing 324 and the conduit interface 148. For example, the conduit interface 148 may be in fluid communication with the enclosure 172 or the sealed space 174 through the aperture 170 in the sealing member 140. In some embodiments, the conduit 196 may be inserted into the dressing 324 through the aperture 170 in the sealing member 140 to provide fluid communication with the reduced-pressure source 128 without use of the conduit interface 148. The reduced-pressure source 128 may also be directly coupled in fluid communication with the dressing 324 or the sealing member 140 without use of the conduit 196. In some embodiments, the conduit 196 may be, for example, a flexible polymer tube. A distal end of the conduit 196 may include a coupling 198 for attachment to the reduced-pressure source 128.

The conduit 196 may have a secondary hydrophobic filter 199 disposed in the internal lumen 197 such that fluid communication between the reduced-pressure source 128 and the dressing 324 is provided through the secondary hydrophobic filter 199. The secondary hydrophobic filter 199 may be, for example, a porous, sintered polymer cylinder sized to fit the dimensions of the internal lumen 197 to substantially preclude liquid from bypassing the cylinder. The secondary hydrophobic filter 199 may also be treated with an absorbent material adapted to swell when brought into contact with liquid to block the flow of the liquid. The secondary hydrophobic filter 199 may be positioned at any location within the internal lumen 197. However, positioning the secondary hydrophobic filter 199 within the internal lumen 197 closer toward the reduced-pressure source 128, rather than the dressing 324, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application.

Figure 19:
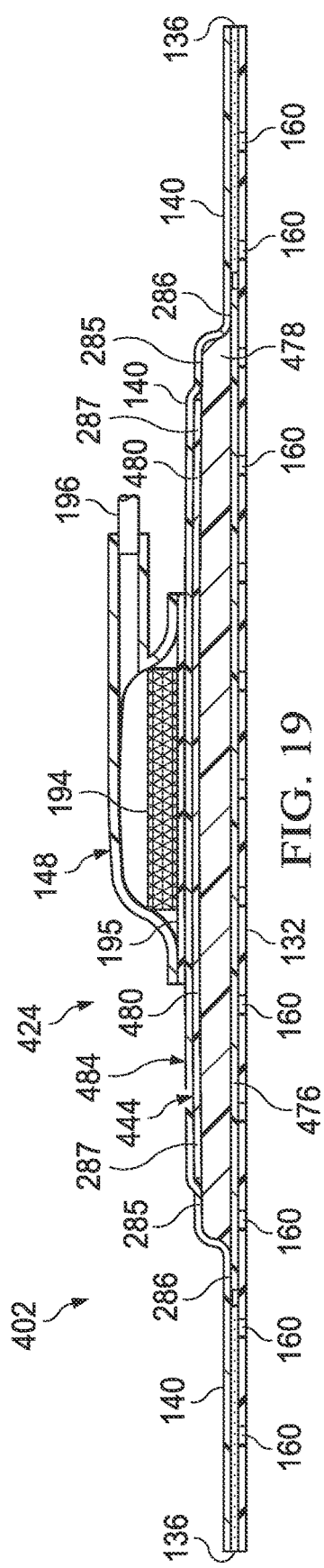
FIG. 19 is a cut-away view of another illustrative example of a dressing and a fluid management assembly suitable for use with the system of FIG. 13.
Figure 20:
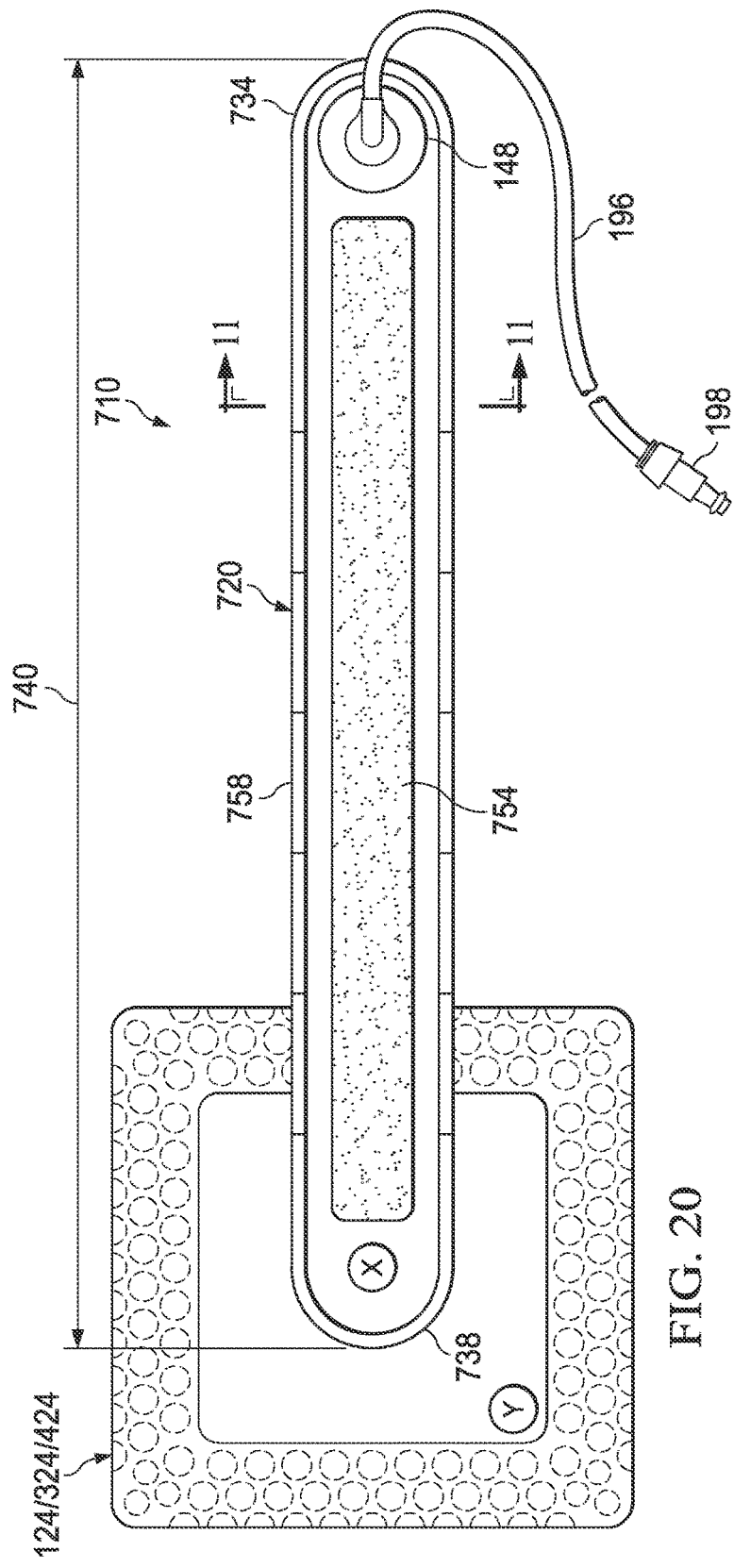
FIG. 20 is a plan view of an illustrative example of a bridge assembly suitable for use with the system and the dressing of FIG. 13.

Referring to FIG. 19, another embodiment of a fluid management assembly 444 suitable for use with the dressing 424 and the system 402 is shown. The fluid management assembly 444 may include one or more dressing wicking layers 484 such as a first dressing wicking layer 476, a second dressing wicking layer 478, and a third dressing wicking layer 480 comprised of substantially the same materials and properties as those described above in connection with the fluid management assembly 144. Thus, the first dressing wicking layer 476, the second dressing wicking layer 478, and the third dressing wicking layer 480 may be analogous to the first dressing wicking layer 376, the second dressing wicking layer 378, and the third dressing wicking layer 381, respectively.

In the fluid management assembly 444, the third dressing wicking layer 480 may have a peripheral portion 287. The third dressing wicking layer 480 and the peripheral portion 287 of the first dressing wicking layer 476 may be positioned in contact with the sealing member 140. The second dressing wicking layer 478 may have a peripheral portion 285 extending beyond the peripheral portion 287 of the third dressing wicking layer 480. The second dressing wicking layer 478 may be positioned adjacent to or proximate to the first dressing wicking layer 280 such that the peripheral portion 285 of the second dressing wicking layer 478 is in contact with the sealing member 140 surrounding the peripheral portion 287 of the third dressing wicking layer 480. Similarly, the first dressing wicking layer 476 may have a peripheral portion 286 extending beyond the peripheral portion 285 of the second dressing wicking layer 478. The first dressing wicking layer 476 may be positioned adjacent to or proximate to the second dressing wicking layer 478 such that the peripheral portion 286 of the first dressing wicking layer 476 is in contact with the sealing member 140 surrounding the peripheral portion 285 of the second dressing wicking layer 478. Further, the first dressing wicking layer 476 may be positioned adjacent to or proximate to the base layer 132. Thus, at least the peripheral portion 287, the peripheral portion 285, and the peripheral portion 286 may be coupled to the sealing member 140, such as, for example, by an adhesive coating disposed on a surface of the sealing member 140 facing the base layer 132. The adhesive coating may be analogous to the adhesive 136 that may be applied across the surface of the sealing member 140 facing the base layer 132. The third dressing wicking layer 480, the second dressing wicking layer 478, and the first dressing wicking layer 476 may respectively have increasing surface areas to enhance contact with the adhesive coating described above. In other embodiments, the fluid management assembly 444 may include any number of absorbent layers and wicking layers for treating a particular tissue site.

In operation, according to some illustrative embodiments, the interface manifold 120 may be disposed against or proximate to the tissue site 104. The dressing 324, 424 may be applied over or covering the interface manifold 120 and the tissue site 104 to form the sealed space 174. For example, the base layer 132 may be applied covering the interface manifold 120 and tissue surrounding the tissue site 104. The materials described above for the base layer 132 may have a tackiness that may hold the dressing 324 or 424 initially in position. The tackiness may be such that if an adjustment is desired, the dressing 324, 424 may be removed and reapplied. Once the dressing 324, 424 is in the desired position, a force may be applied, such as hand pressure, on a side of the sealing member 140 facing outward or opposite the tissue site 104. The force applied to the sealing member 140 may cause at least some portion of the adhesive 136 to penetrate or extend through the plurality of apertures 160 and into contact with tissue surrounding the tissue site 104, such as the epidermis 106, to releasably adhere the dressing 324, 424 about the tissue site 104. In this manner, the configuration of the dressing 324, 424 described herein may provide an effective and reliable seal against challenging anatomical surfaces, such as an elbow or heal, at and around the tissue site 104. Further, the dressing 324, 424 may permit re-application or re-positioning to, for example, correct air leaks caused by creases and other discontinuities in the dressing 324, 424 and the tissue site 104. The ability to rectify leaks may increase the reliability of the therapy and reduce power consumption.

As the dressing 324, 424 comes into contact with fluid from the tissue site 104, the fluid may move through the apertures 160 toward the fluid management assembly 344, 444. The fluid management assembly 344, 444 may wick or otherwise move the fluid away from the tissue site 104, and through the interface manifold 120, if equipped. As described above, the interface manifold 120 may be adapted to communicate fluid from the tissue site 104 rather than store the fluid. Thus, the fluid management assembly 344, 444 may be adapted to wick, pull, draw, or otherwise attract fluid from the tissue site 104 through the interface manifold 120. In the fluid management assembly 344, 444 the fluid may initially come into contact with the first dressing wicking layer 376, 476. The first dressing wicking layer 376, 476 may distribute the fluid laterally along the surface of the first dressing wicking layer 376, 476 for absorption or removal from the dressing 324, 424. Similarly, fluid may come into contact with the third dressing wicking layer 381, 480 and may be distributed laterally along the surface of the third dressing wicking layer 381, 480 for absorption or removal from the dressing 324, 424.

Figure 21:
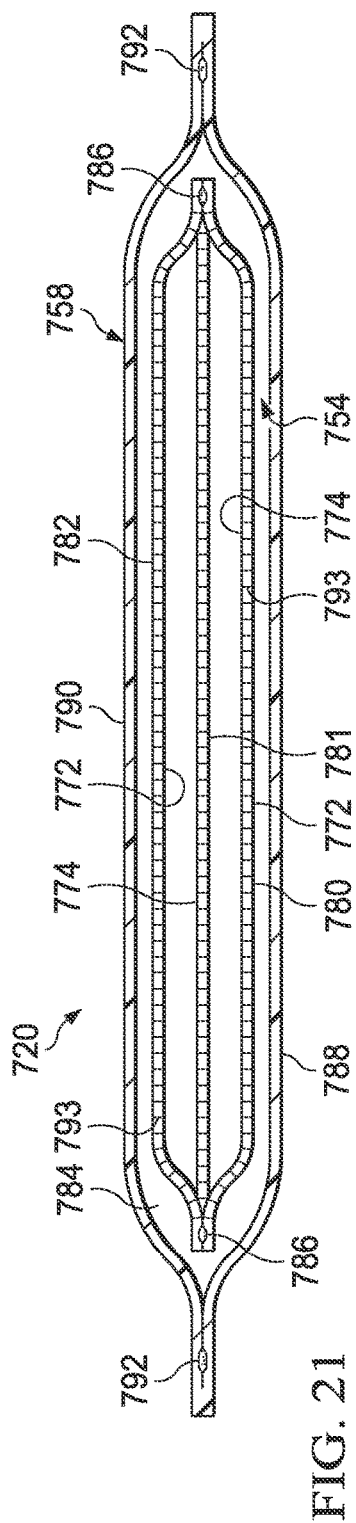
FIG. 21 is a cross-section of an illustrative example of a bridge shown with the bridge assembly of FIG. 20, taken at lines 11-11.
Figure 22:
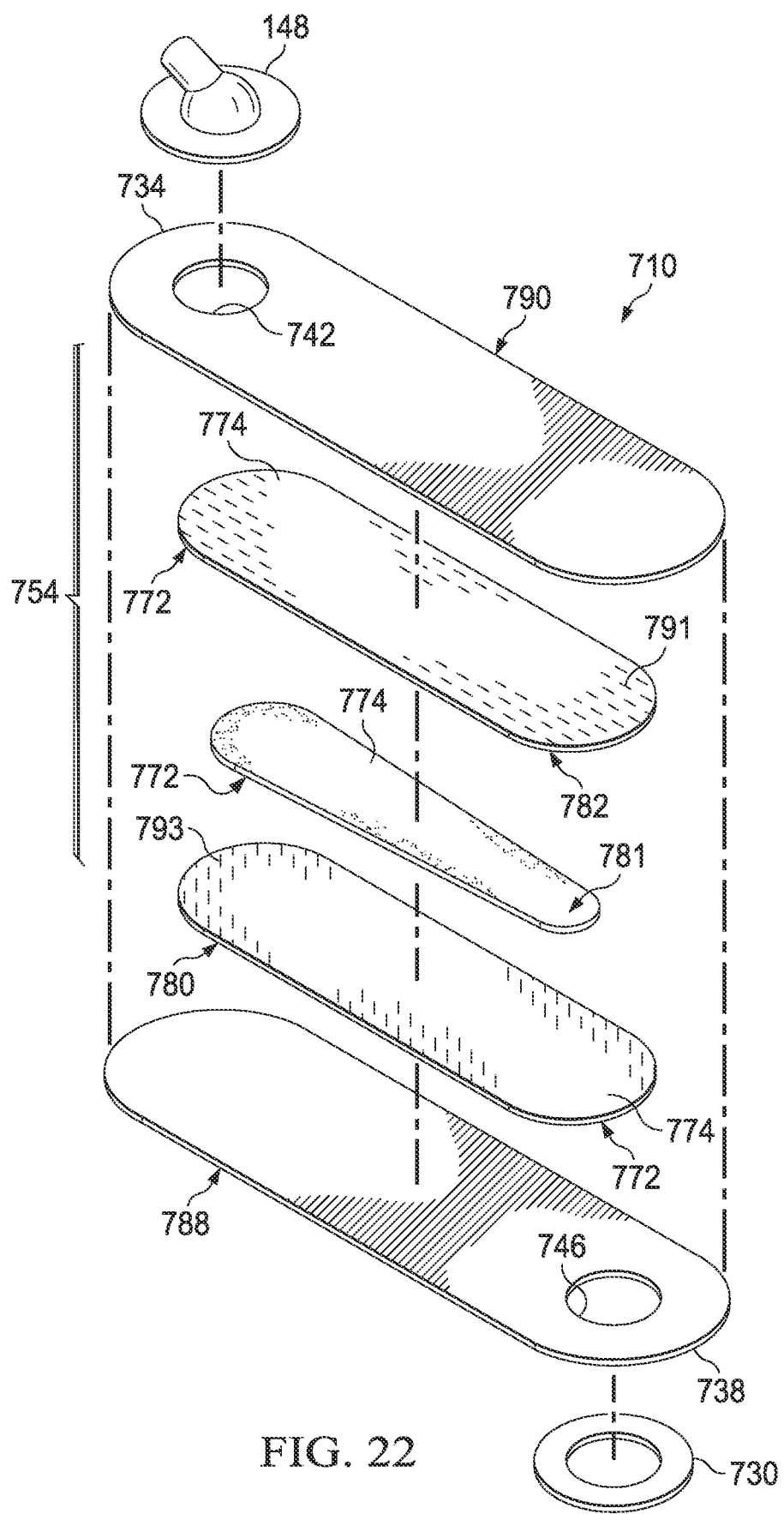
FIG. 22 is an exploded view of the bridge assembly of FIG. 20.

Referring to FIGS. 21-23, in some embodiments, a bridge assembly 710 may extend away from the tissue site 104 and the dressing 124, 324, 424 to define a fluid passageway between the tissue site 104 and the reduced-pressure source 128. For example, the bridge assembly 710 may be coupled in fluid communication between the dressing 124, 324, 424 and the reduced-pressure source 128. However, other applications for the bridge assembly 710 are possible. In some embodiments, the bridge assembly 710 may include a bridge 720, a sealing apparatus 730, and the conduit interface 148.

The bridge 720 may include a receiving end 734 separated or spaced apart from a transmitting end 738 by a length 740. The receiving end 734 may have a receiving end aperture 742, and the transmitting end 738 may have a transmitting end aperture 746. The receiving end 734 and the receiving end aperture 742 may be in fluid communication with the transmitting end 738 and the transmitting end aperture 746 through the length 740 of the bridge 720.

The conduit interface 148 may be adapted to be fluidly coupled to the receiving end 734 of the bridge 720 through, for example, the receiving end aperture 742. Thus, the conduit interface 148 may be in fluid communication with the transmitting end 738 through the length 740 of the bridge 720. The sealing apparatus 730 may be positioned about the transmitting end aperture 746 and between the transmitting end 738 and the dressing 124, 324, 424 for coupling the transmitting end 738 to the dressing 124, 324, 424 and in fluid communication with the dressing 124 through the transmitting end aperture 746. Thus, the conduit interface 148 may be positioned in fluid communication with the dressing 124, 324, 424 through the bridge 720. The sealing apparatus 730 may be any suitable device for making the connections described above, such as, without limitation, an adhesive ring or weld.

In some embodiments, the bridge 720 may include one or more wicking layers 754, and a bridge sealing member 758. The bridge sealing member 758 may extend along the length 740 of the bridge 720. Further, the bridge sealing member 758 may define an internal passageway 784. The one or more wicking layers 754 may be disposed within the internal passageway 784 of the bridge sealing member 758. In some embodiments, the bridge sealing member 758 may entirely surround the one or more wicking layers 754. Further, in some embodiments, the bridge sealing member 758 may encapsulate the one or more wicking layers 754.

In some embodiments, the one or more wicking layers 754 may include at least one of a first wicking layer 780, a second wicking layer 781, or a third wicking layer 782. In some embodiments, the first wicking layer 780, the second wicking layer 781, and the third wicking layer 782 may be referred to as a first bridge wicking layer, a second bridge wicking layer, and a third bridge wicking layer, respectively. Each of the one or more wicking layers 754 may extend along the length 740 of the bridge 720, and may be disposed within the internal passageway 784 that may be defined by the bridge sealing member 758. The first wicking layer 780, the second wicking layer 781, and the third wicking layer 782 may each be comprised of the same materials recited above for the first dressing wicking layer 176 and the second dressing wicking layer 180.

A periphery or edge of the first wicking layer 780 may be coupled to a periphery or edge of the second wicking layer 781 in any suitable manner, such as, for example, by a weld 786, to define the internal passageway 784 of the bridge envelope 750. A periphery or edge of the second wicking layer 781 may be coupled to a periphery or edge of the third wicking layer 782 in any suitable manner, such as, for example, by a weld 786, to define the internal passageway 784 of the bridge sealing member 758. The second wicking layer 781 may be positioned between the first wicking layer 780 and the third wicking layer 782. In some embodiments, the one or more wicking layers 754 (such as the first wicking layer 780, the second wicking layer 781, and the third wicking layer 782) may be positioned and sealed between the first sealing layer 788 and the second sealing layer 790 without a weld (such as weld 786) coupling the one or more wicking layers 754. In some embodiments, the one or more wicking layer 754 may be separated from each other or may be held together using The first wicking layer 780, the second wicking layer 781, and the third wicking layer 782 may each include a fluid acquisition surface 772 and a fluid distribution surface 774. The fluid distribution surface 774 may be positioned on an opposite side of the first wicking layer 780, the second wicking layer 781, and the third wicking layer 782 from the fluid acquisition surface 772. The fluid acquisition surface 772 of each of the first wicking layer 780, the second wicking layer 781, and the third wicking layer 782 may face in a direction of the first sealing layer 788. Further, the fluid distribution surface 774 of each of the first wicking layer 780, the second wicking layer 781, and the third wicking layer 782 may face in a direction of the second sealing layer 790. The fluid acquisition surface 772 of each of the first wicking layer 780, the second wicking layer 781, and the third wicking layer 782 may face in a direction of the second sealing layer 790. The fluid distribution surface 774 of each of the first wicking layer 780, the second wicking layer 781, and the third wicking layer 782 may face in a direction of the first sealing layer 788. In some embodiments, a fluid acquisition surface 772 of the first wicking layer 780 may face a fluid acquisition surface 772 of the second wicking layer 781. In some embodiments, a fluid acquisition surface 772 of the second wicking layer 781 may face a fluid acquisition surface 772 of the third wicking layer 782. In some embodiments, a fluid distribution surface 774 of the first wicking layer 780 may face a fluid distribution surface 774 of the second wicking layer 781. In some embodiments, a fluid distribution surface 774 of the second wicking layer 781 may face a fluid distribution surface 774 of the third wicking layer 782.

In some embodiments, at least a portion of the first wicking layer 780 may be in direct contact with at least a portion of the second wicking layer 781. In some embodiments, at least a portion of the first wicking layer 780 may be spaced apart or separated from the second wicking layer 781 by an internal volume 760. In some embodiments, at least a portion of the second wicking layer 781 may be in direct contact with at least a portion of the third wicking layer 782. In some embodiments, at least a portion of the second wicking layer 781 may be spaced apart or separated from the third wicking layer 782 by an internal volume 706. In some embodiments, the fluid distribution surface 774 may include a plurality of longitudinal fibers 791 oriented substantially in a longitudinal direction along the length 740 of the bridge 720. Further, in some embodiments, the fluid acquisition surface 772 may include a plurality of vertical fibers 793 oriented substantially normal relative to the longitudinal fibers 791.

In some embodiments, the one or more wicking layers 754 may include a first set of one or more bridge wicking layers and a second set of one or more bridge wicking layers. The first set of one or more bridge wicking layers and the second set of one or more bridge wicking layers may each extend along the length 740 of the storage bridge 720, and may be disposed within an internal passageway 784 that may be defined by the bridge sealing member 758. A periphery or edge of at least one bridge wicking layer of the first set of one or more bridge wicking layers may be coupled to a periphery or edge of at least one bridge wicking layer of the second set of one or more bridge wicking layers in any suitable manner, such as, for example, by a weld 786, to define the internal volume 760 of the bridge envelope 750. A bridge absorbent (such as bridge absorbent 354) may be positioned between the first set of one or more bridge wicking layers and the second set of one or more bridge wicking layers. At least one bridge wicking layer of the first set of one or more bridge wicking layers and at least one bridge wicking layer of the second set of one or more bridge wicking layers may each include the fluid acquisition surface 772 and the fluid distribution surface 774. The fluid distribution surface 774 may be positioned on an opposite side of the at least one bridge wicking layer of the first set of one or more bridge wicking layers and the at least one bridge wicking layer of the second set of one or more bridge wicking layers from the fluid acquisition surface 772. Further, the fluid distribution surface 774 of the at least one bridge wicking layer of the first set of one or more bridge wicking layers and the at least one bridge wicking layer of the second set of one or more bridge wicking layers may face the bridge absorbent (such as bridge absorbent 354). In some embodiments, at least a portion of the bridge absorbent may be spaced apart or separated from the fluid distribution surface 774 of the at least one bridge wicking layer of the first set of one or more bridge wicking layers and the at least one bridge wicking layer of the second set of one or more bridge wicking layers.

In some embodiments, the internal passageway 784 may house a film, a first wicking layer, a second wicking layer. The film may be a base layer of adhesive coated polyurethane (PU) film. The adhesive coated on the film may adhere the first wicking layer to an inner surface of the bridge sealing member 758. The first wicking layer may be stacked or placed below or underneath the second wicking layer such that fluid (such a fluid of exudate) is communicated from the first wicking layer to the second wicking layer and out the conduit interface 148. The first wicking layer may have a wider base and a higher density relative to the second wicking layer. The first wicking layer may have a greater thickness (such as 50 mm) relative to the second wicking layer thickness (such as 20 mm). The first wicking layer may include a profile to spread the fluid out over an entire surface of the first wicking layer to increase evaporation. The second wicking layer may be used to pull fluid from the wound towards to the conduit interface 148. In some embodiments, the second wicking layer may alternatively or additionally include a profile like the profile of the first wicking layer to spread fluid out over an entire surface of the second wicking layer. The profile of the second wicking layer may also be used to increase evaporation.

The bridge sealing member 758 may define the internal passageway 784. The internal passageway 784 may be in fluid communication between the receiving end 734 and the transmitting end 738 of the bridge 720. In some embodiments, the bridge sealing member 758 may entirely surround the one or more wicking layers 754. In some embodiments, the bridge sealing member 758 may sealingly enclose the one or more wicking layers 754 between the receiving end 734 and the transmitting end 738 of the bridge 720.

The bridge sealing member 758 may be comprised of similar materials described herein for the dressing sealing member 140. For example, in some embodiments, the bridge sealing member 758 may comprise a substantially liquid impermeable film. Further, in some embodiments, the bridge sealing member 758 may comprise a vapor permeable film. Further, in some embodiments, the bridge sealing member 758 may comprise a breathable film. Additional examples of materials suitable for the bridge sealing member 758 may include, without limitation, a polyurethane (PU) drape or film such as Scapa Bioflex 130 polyurethane Film®; films formed from polymers, such as polyester and co-polyester; polyamide; polyamide/block polyether; acrylics; vinyl esters; polyvinyl alcohol copolymers; films with and without adhesive; and high Moisture Vapor Transfer Rate (MVTR) films, such as, for example, an INSPIRE 2305 polyurethane drape. High MVTR films may provide for evaporation of condensate, which may occur around the entire exterior surface of the bridge 720. In this manner, capacity, fluid handling, and evaporative properties of the bridge 720 may be enhanced or improved due at least to increased surface area and air movement provided around all sides and portions of the exterior surface of the bridge 720.

The bridge sealing member 758 may comprise a nonwoven material or structure such as, without limitation, a polyester, co-polyester, polyolefin, cellulosic fiber, and combinations or blends of the foregoing materials. In some embodiments, the bridge sealing member 758 may comprise LIBELTEX TDL4 or LIBELTEX TDL2, or any of the materials recited above for the first dressing wicking layer 176 and the second dressing wicking layer 180. Further, in some embodiments, the bridge sealing member 758 may comprise laminations with fiber or foam structures.

In some embodiments, the bridge sealing member 758 may include the first sealing layer 788 and the second sealing layer 790. A first periphery or edge of the first sealing layer 788 may be coupled to a second periphery or edge of the second sealing layer 790 around the bridge envelope 750 in any suitable manner, such as, for example, by a weld 792 for forming the bridge sealing member 758 and encapsulating the bridge envelope 750 therein. In other embodiments, the bridge sealing member 758 may be formed from a single layer of material.

In operation, the reduced-pressure source 128 may be fluidly coupled to the receiving end 734 of the bridge 720. For example, the conduit interface 148 may be fluidly coupled to the receiving end 734, and the conduit 196 may be fluidly coupled between the conduit interface 148 and the reduced-pressure source 128 analogous to the previously described embodiments. The transmitting end 738 of the bridge 720 may be fluidly coupled to the dressing 124 as described herein. The reduced-pressure source 128 may be activated to provide reduced pressure to the dressing 124 through the bridge 720, which may draw, wick, or pull fluids from the tissue site 104 and the dressing 124 into the bridge 720.

As fluid enters the bridge 720 through the transmitting end 738, the fluid may communicate through the internal passageway 784 and contact the fluid acquisition surface 772 of the first wicking layer 780. The fluid acquisition surface 772 of the first wicking layer 780 may receive the fluid so that the fluid may be transported through the first wicking layer 780. Subsequently, the fluid distribution surface 774 of the first wicking layer 780 may transmit the fluid from the first wicking layer 780. In some embodiments, the fluid distribution surface 774 of the first wicking layer 780 may transmit the fluid directly to the receiving end 734. In some embodiments, the fluid distribution surface 774 of the first wicking layer 780 may transmit fluid into the internal volume 760. In some embodiments, the fluid distribution surface 774 of the first wicking layer 780 may transmit the fluid to the receiving end 734 through the internal volume 760. In some embodiments, the fluid distribution surface 774 of the first wicking layer 780 may transmit fluid to the fluid acquisition surface 772 of the second wicking layer 781.

As fluid is transmitted from the fluid distribution surface 774 of the first wicking layer 780, the fluid may contact the fluid acquisition surface 772 of the second wicking layer 781. The fluid acquisition surface 772 of the second wicking layer 781 may receive the fluid so that the fluid may be transported through the second wicking layer 781. Subsequently, the fluid distribution surface 774 of the second wicking layer 781 may transmit the fluid from the second wicking layer 781. In some embodiments, the fluid distribution surface 774 of the second wicking layer 781 may transmit the fluid directly to the receiving end 734. In some embodiments, the fluid distribution surface 774 of the second wicking layer 781 may transmit fluid into the internal volume 760. In some embodiments, the fluid distribution surface 774 of the second wicking layer 781 may transmit the fluid to the receiving end 734 through the internal volume 760. In some embodiments, the fluid distribution surface 774 of the second wicking layer 781 may transmit fluid to the fluid acquisition surface 772 of the third wicking layer 782.

As fluid is transmitted from the fluid distribution surface 774 of the second wicking layer 781, the fluid may contact the fluid acquisition surface 772 of the third wicking layer 782. The fluid acquisition surface 772 of the third wicking layer 782 may receive the fluid so that the fluid may be transported through the third wicking layer 782. Subsequently, the fluid distribution surface 774 of the third wicking layer 782 may transmit the fluid from the third wicking layer 782. In some embodiments, the fluid distribution surface 774 of the third wicking layer 782 may transmit the fluid directly to the receiving end 734.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. For example, an absorbent layer, such as absorbent layer 184 discussed herein, may be included within the bridge assembly 710. As such, the benefits and advantages described above may relate to one embodiment or may relate to several embodiments. Further, the steps of the methods described herein may be carried out in any suitable order, or simultaneously where appropriate.

It should be understood, that dressings as discussed herein may include only one or more wicking layers (i.e. a dressing without an absorbent layer) and that a bridge as discussed herein in fluid communication with such dressing may include only one or more wicking layers (i.e. a bridge without an absorbent layer). It should also be understood, that that dressings as discussed herein may include only one or more wicking layers (i.e. a dressing without an absorbent layer) and that a bridge as discussed herein in fluid communication with such dressing may include one or more wicking layers and an absorbent layer. In addition, it should be understood, that dressings as discussed herein may include one or more wicking layers and an absorbent layer and that a bridge as discussed herein in fluid communication with such dressing may include only one or more wicking layers (i.e. a bridge without an absorbent layer).

Among other benefits described above, the storage bridge 320 may reduce power consumption, leakage, and other challenges that may be associated with fluid head pressure caused by a static column of fluid that can reside in a conventional tube or similar structure providing fluid communication between a dressing and a reduced-pressure source. Further, a mass of fluid removed from a tissue site may be moved away from the surface of the tissue site. The storage bridge 320 may also provide a low-profile and conformable solution for providing fluid communication with a tissue site, which may enhance patient comfort.

In addition, a system with dressings and/or bridges with one or more wicking layers and without absorbents may provide a low profile dressing and bridge so that a patient may discretely wear such a system, for example, by securing it to a tissue site with one or more bandages. In addition, a system with dressings and/or bridges with one or more wicking layers and without absorbents may be used with a manual pump or hand pump to remove fluid from a tissue site due to having relatively less air taken to be taken up by a canister of or in fluid communication with the manual pump or hand pump. This may be due at least in part to the low profile created by the one or more wicking layers. Further, a system with dressings and/or bridges with one or more wicking layers and without absorbents may have relatively less head pressure when reduced pressure is applied by a manual pump or hand pump. A system with dressings and/or bridges with one or more wicking layers and without absorbents may also extend the life of the system and increase mobility by a patient.

What is claimed is:

1. A bridge for treating a tissue site, the bridge comprising:
    a receiving end and a transmitting end separated by a length;
    a bridge sealing member extending along the length and defining an internal passageway in fluid communication between the receiving end and the transmitting end, the bridge sealing member comprising a first sealing layer and a second sealing layer positioned opposite the first sealing layer; and
    one or more bridge wicking layers disposed within the bridge sealing member, at least a portion of each of the one or more bridge wicking layers spaced apart from the bridge sealing member;

wherein the one or more bridge wicking layers comprise a first bridge wicking layer and a second bridge wicking layer, wherein the first bridge wicking layer has a surface area that is greater than a surface area of the second bridge wicking layer, wherein the first bridge wicking layer has a density that is greater than a density of the second bridge wicking layer, and wherein the first bridge wicking layer is adapted to be positioned underneath the second bridge wicking layer.

2. The bridge of claim 1, further comprising an absorbent disposed within the bridge sealing member, at least a portion of the absorbent spaced apart from the first sealing layer and the second sealing layer of the bridge sealing member.

3. The bridge of claim 1, wherein the bridge sealing member entirely surrounds the one or more bridge wicking layers.

4. The bridge of claim 1, wherein the one or more bridge wicking layers comprises a first bridge wicking layer, a second bridge wicking layer, and a third bridge wicking layer, wherein a periphery of the first bridge wicking layer is coupled to a periphery of the third bridge wicking layer, and wherein the second bridge wicking layer is disposed between the first bridge wicking layer and the third bridge wicking layer.

5. The bridge of claim 4, wherein each of the one or more bridge wicking layers is comprised of a non-woven material.

6. The bridge of claim 4, wherein each of the one or more bridge wicking layers comprises a fluid acquisition surface and a fluid distribution surface positioned opposite the fluid acquisition surface, wherein the fluid distribution surface of each of the one or more bridge wicking layers faces a first direction, and wherein the fluid acquisition surface of each of the one or more bridge wicking layers faces a second direction.

7. The bridge of claim 1, wherein the bridge sealing member comprises a substantially liquid impermeable and vapor permeable film.

\* \* \* \* \*